(12) United States Patent
Shirai et al.

(10) Patent No.: US 9,347,944 B2
(45) Date of Patent: May 24, 2016

(54) METHOD FOR DETECTING PNEUMONIA CAUSATIVE BACTERIA USING NUCLEIC ACID CHROMATOGRAPHY

(75) Inventors: Mutsunori Shirai, Ube (JP); Takayuki Ezaki, Gifu (JP); Tsukasa Hayashi, Tokyo (JP); Takeshi Ujiiye, Tokyo (JP); Makoto Ganaha, Tokyo (JP); Shigekazu Yamamoto, Tokyo (JP)

(73) Assignee: Yamaguchi Technology Licensing Organization, Ltd., Yamaguchi (JP)

( * ) Notice: Subject to any disclaimer, the term of this patent is extended or adjusted under 35 U.S.C. 154(b) by 557 days.

(21) Appl. No.: 13/637,815

(22) PCT Filed: Mar. 30, 2011

(86) PCT No.: PCT/JP2011/001934
§ 371 (c)(1),
(2), (4) Date: Sep. 27, 2012

(87) PCT Pub. No.: WO2011/122034
PCT Pub. Date: Oct. 6, 2011

(65) Prior Publication Data
US 2013/0023443 A1 Jan. 24, 2013

(30) Foreign Application Priority Data

Mar. 31, 2010 (JP) .................................. 2010-083823
Mar. 31, 2010 (JP) .................................. 2010-083836

(51) Int. Cl.
*C12Q 1/68* (2006.01)
*G01N 33/569* (2006.01)

(52) U.S. Cl.
CPC .......... *G01N 33/56933* (2013.01); *C12Q 1/689* (2013.01); *C12Q 1/6816* (2013.01); *C12Q 1/6865* (2013.01); *G01N 33/56911* (2013.01); *G01N 33/56916* (2013.01); *G01N 33/56938* (2013.01); *G01N 33/56944* (2013.01); *C12Q 2600/112* (2013.01); *C12Q 2600/156* (2013.01)

(58) Field of Classification Search
None
See application file for complete search history.

(56) References Cited

U.S. PATENT DOCUMENTS

| 6,559,294 | B1 * | 5/2003 | Griffais et al. ............... 536/23.1 |
| 7,553,626 | B2 | 6/2009 | Oh et al. |
| 2002/0086289 | A1 * | 7/2002 | Straus ............................. 435/6 |

FOREIGN PATENT DOCUMENTS

| CA | 1287558 C | 8/1991 |
| EP | 0 139 489 A2 | 5/1985 |
| EP | 2 078 756 A1 | 7/2009 |
| FR | WO2005049642 | * 6/2005 ........... C07K 14/195 |
| JP | 60-093355 A | 5/1985 |
| JP | 62-205800 A | 9/1987 |
| JP | 2005-110545 A | 4/2005 |
| JP | 2006-174837 A | 7/2006 |
| JP | 2006-180878 A | 7/2006 |
| JP | 2006-201062 A | 8/2006 |
| JP | 4235645 B2 | 12/2008 |
| JP | 2009-039046 A | 2/2009 |
| JP | 4268944 B2 | 2/2009 |
| JP | 2009-240207 A | 10/2009 |
| WO | WO 2008/041354 A1 | 4/2008 |
| WO | WO 2008/105814 A2 | 9/2008 |
| WO | WO 2008/140494 A2 | 11/2008 |
| WO | WO 2009/057330 A1 | 5/2009 |

OTHER PUBLICATIONS

Loens et al. (J of Microbiol Methods, 2008, vol. 73, p. 257-262).*
Dandekar et al. (Nucleic Acids Res. 2000, 28 (17), 3278-3288).*
Lowe et al. (Nucleic Acids Research, vol. 18, No. 7, p. 1757-1761, 1990).*
Ezaki et al., "New Development of a genetic test method for exhaustively and rapidly detecting viable cells using DnaJ genes," Journal of Japanese Society for Bacteriology, 2009, 64(1):105, WS21-3, with English translation.
Ujiie, Takeshi, "'Nucleic Acid Chromatograpy' a simple tool for genetic testing" ("Kanben na Idenshi Kensa no Tool 'Kakusan Chromao-ho'"), Rinsho Kagaku, Jan. 2007, 36:19-24, with English translation of indicated portions, 2 pages.
Carter et al., "Lateral flow microarrays: a novel platform for rapid nucleic acid detection based on miniaturized lateral flow chromatography," Nucleic Acids Research, Apr. 22, 2007, 35(10):e74, 11 pages.
Kalogianni et al., "Dry reagent dipstick test combined with 23S rRNA PCR for molecular diagnosis of bacterial infection in arthroplasty," Analytical Biochemistry, Jan. 24, 2007, 361:169-175.
Kalogianni et al., "Dipstick-type biosensor for visual detection of DNA with oligonucleotide-decorated colored polystyrene microspheres as reporters," Biosensors and Bioelectronics, Feb. 15, 2009, 24(6):1811-1815.

* cited by examiner

Primary Examiner — Stephanie K Mummert
(74) Attorney, Agent, or Firm — Foley & Lardner LLP

(57) ABSTRACT

Provided are a method and a kit for accurately and rapidly detecting ten types of targeting pneumonia bacteria: *Streptococcus pneumoniae, Haemophilus influenzae, Mycoplasma pneumoniae, Chlamydophila pneumoniae, Legionella pneumophila, Klebsiella pneumoniae, Pseudomonas aeruginosa, Moraxella catarrhalis*, methicillin-resistant *Staphylococcus aureus* (MRSA), and *Staphylococcus aureus*. A set of primer pairs directed to their respective target regions contained in the DnaJ gene, etc., of the ten types of pneumonia causative bacteria is designed for the ten bacterial strains and used to amplify gene products. A set of bacterial strain-specific probe pairs is further designed for the ten bacterial strains such that the probe pairs hybridize with the amplification products via sequences in the respective target regions differing from the sequences hybridized by the set of primer pairs. A first probe-bound labeled high molecular carrier in which plural types of first probes for the pneumonia bacteria are bound to a labeled high molecular carrier and a solid-phase second probe-carrying developing support are used as the set of probe pairs to perform nucleic acid chromatography.

4 Claims, 18 Drawing Sheets

Design of *Moraxella catarrhalis dnaJ* primers

1: Ladder
2: Negative control
3: *Moraxella catarrhalis* GTC 01544
4: *Moraxella catarrhalis* GTC 02090
5: *Moraxella catarrhalis* GTC 10829
6: *Moraxella catarrhalis* GTC 10830
7: *Moraxella catarrhalis* GTC 10831
8: *Moraxella catarrhalis* GTC 10832
9: *Moraxella catarrhalis* GTC 10833
10: *Moraxella catarrhalis* GTC 10834

RNA amplification was confirmed.

Figure 9

|   |   | 1 | 2 | 3 | 4 | 5 | 6 | 7 | 8 | 9 | 10 |
|---|---|---|---|---|---|---|---|---|---|---|---|
| 1 | *S. pneumoniae* |   | — | — | — | — | — | — | — | — | — |
| 2 | *H. influenzae* | — |   | — | — | — | — | — | — | — | — |
| 3 | *M. pneumoniae* | — | — |   | — | — | — | — | — | — | — |
| 4 | *C. pneumoniae* | — | — | — |   | — | — | — | — | — | — |
| 5 | *L. pneumophila* | — | — | — | — |   | — | — | — | — | — |
| 6 | *K. pneumoniae* | — | — | — | — | — |   | — | — | — | — |
| 7 | *P. aeruginosa* | — | — | — | — | — | — |   | — | — | — |
| 8 | *M. catarrhalis* | — | — | — | — | — | — | — |   | — | — |
| 9 | *S. aureus* | — | — | — | — | — | — | — | — |   | — |
| 10 | MRSA | — | — | — | — | — | — | — | — | — |   |

For outpatient        For hospitalized patient

1 *Streptococcus pneumoniae*
2 *Haemophilus influenzae*
3 *Mycoplasma pneumoniae*
4 *Legionella pneumophila*
5 *Chlamydophila pneumoniae*

6 *Pseudomonas aeruginosa*
7 *Klebsiella pneumoniae*
8 *Staphylococcus aureus*
9 Methicillin-resistant *Staphylococcus aureus* (MRSA)
10 *Moraxella catarrhalis*

MR: Methicillin-resistant *Staphylococcus aureus* (MRSA)
Hi: *Haemophilus influenzae*
Lp: *Legionella pneumophila*
Cp: *Chlamydophila pneumoniae*
Sa: *Staphylococcus aureus*
Mo: *Moraxella catarrhalis*
Sp: *Streptococcus pneumoniae*
Kp: *Klebsiella pneumoniae*
Pa: *Pseudomonas aeruginosa*
Mp: *Mycoplasma pneumoniae*

Figure 16

|   |                | 1 | 2 | 3 | 4 | 5 | 6 | 7 | 8 | 9 | 10 |
|---|----------------|---|---|---|---|---|---|---|---|---|----|
| 1 | S. pneumoniae  | O | — | — | — | — | — | — | — | — | —  |
| 2 | H. influenzae  | — | O | — | — | — | — | — | — | — | —  |
| 3 | M. pneumoniae  | — | — | O | — | — | — | — | — | — | —  |
| 4 | C. pneumoniae  | — | — | — | O | — | — | — | — | — | —  |
| 5 | L. pneumophila | — | — | — | — | O | — | — | — | — | —  |
| 6 | K. pneumoniae  | — | — | — | — | — | O | — | — | — | —  |
| 7 | P. aeruginosa  | — | — | — | — | — | — | O | — | — | —  |
| 8 | M. catarrhalis | — | — | — | — | — | — | — | O | — | —  |
| 9 | S. aureus      | — | — | — | — | — | — | — | — | O | —  |
| 10| MRSA           | — | — | — | — | — | — | — | — | — | O  |

Mp: Mycoplasma pneumoniae
Hi: Haemophilus influenzae
Sp: Streptococcus pneumoniae
Cp: Chlamydophila pneumoniae
Lp: Legionella pneumophila
Mo: Moraxella catarrhalis
MR: Methicillin-resistant Staphylococcus aureus (MRSA)
Sa: Staphylococcus aureus
Pa: Pseudomonas aeruginosa
Kp: Klebsiella pneumoniae

SEQUENCE LISTING

```
<160> NUMBER OF SEQ ID NOS: 57

<210> SEQ ID NO 1
<211> LENGTH: 25
<212> TYPE: DNA
<213> ORGANISM: Artificial
<220> FEATURE:
<223> OTHER INFORMATION: probe

<400> SEQUENCE: 1
acgcacgagt attgcacgaa taacc                                          25

<210> SEQ ID NO 2
<211> LENGTH: 25
<212> TYPE: DNA
<213> ORGANISM: Artificial
<220> FEATURE:
<223> OTHER INFORMATION: probe

<400> SEQUENCE: 2
aaacttgtcc gcattgccac ggttc                                          25

<210> SEQ ID NO 3
<211> LENGTH: 25
<212> TYPE: DNA
<213> ORGANISM: Artificial
<220> FEATURE:
<223> OTHER INFORMATION: probe

<400> SEQUENCE: 3
aggccaaaca caagtgtaag acttg                                          25
```

```
<210> SEQ ID NO 4
<211> LENGTH: 25
<212> TYPE: DNA
<213> ORGANISM: Artificial
<220> FEATURE:
<223> OTHER INFORMATION: probe

<400> SEQUENCE: 4
atcttgtgaa acctgttctg gtcaa                                   25

<210> SEQ ID NO 5
<211> LENGTH: 25
<212> TYPE: DNA
<213> ORGANISM: Artificial
<220> FEATURE:
<223> OTHER INFORMATION: probe

<400> SEQUENCE: 5
gaagttgaaa ttaccgttcc aagac                                   25

<210> SEQ ID NO 6
<211> LENGTH: 25
<212> TYPE: DNA
<213> ORGANISM: Artificial
<220> FEATURE:
<223> OTHER INFORMATION: probe

<400> SEQUENCE: 6
gtggtggaga cgccggtggg gctga                                   25

<210> SEQ ID NO 7
<211> LENGTH: 20
<212> TYPE: DNA
<213> ORGANISM: Artificial
<220> FEATURE:
<223> OTHER INFORMATION: probe

<400> SEQUENCE: 7
ggtgaccggt gtggtgccgg                                         20

<210> SEQ ID NO 8
<211> LENGTH: 25
<212> TYPE: DNA
<213> ORGANISM: Artificial
<220> FEATURE:
<223> OTHER INFORMATION: probe

<400> SEQUENCE: 8
ggttgcgcgt ttttcaggat cactg                                   25

<210> SEQ ID NO 9
<211> LENGTH: 24
<212> TYPE: DNA
<213> ORGANISM: Artificial
<220> FEATURE:
<223> OTHER INFORMATION: probe

<400> SEQUENCE: 9
agaccgaaac aatgtggaat tggc                                    24

<210> SEQ ID NO 10
<211> LENGTH: 26
<212> TYPE: DNA
<213> ORGANISM: Artificial
<220> FEATURE:
```

```
<223> OTHER INFORMATION: probe

<400> SEQUENCE: 10
catgatcaaa cctggtcaag aacttg                                          26

<210> SEQ ID NO 11
<211> LENGTH: 26
<212> TYPE: DNA
<213> ORGANISM: Artificial
<220> FEATURE:
<223> OTHER INFORMATION: probe

<400> SEQUENCE: 11
tgccgaaaac gcttgataca gggagt                                          26

<210> SEQ ID NO 12
<211> LENGTH: 26
<212> TYPE: DNA
<213> ORGANISM: Artificial
<220> FEATURE:
<223> OTHER INFORMATION: probe

<400> SEQUENCE: 12
ctctggggct gaaaaaggtt ctaaag                                          26

<210> SEQ ID NO 13
<211> LENGTH: 25
<212> TYPE: DNA
<213> ORGANISM: Artificial
<220> FEATURE:
<223> OTHER INFORMATION: probe

<400> SEQUENCE: 13
agaatcaacg ctccatcttt ggtac                                           25

<210> SEQ ID NO 14
<211> LENGTH: 25
<212> TYPE: DNA
<213> ORGANISM: Artificial
<220> FEATURE:
<223> OTHER INFORMATION: probe

<400> SEQUENCE: 14
tcaagggatt aaatcctgcg aacgt                                           25

<210> SEQ ID NO 15
<211> LENGTH: 25
<212> TYPE: DNA
<213> ORGANISM: Artificial
<220> FEATURE:
<223> OTHER INFORMATION: probe

<400> SEQUENCE: 15
caattgaccc ttgaagaagc agcta                                           25

<210> SEQ ID NO 16
<211> LENGTH: 25
<212> TYPE: DNA
<213> ORGANISM: Artificial
<220> FEATURE:
<223> OTHER INFORMATION: probe

<400> SEQUENCE: 16
tgaaacccag accggcaagc tgttc                                           25
```

```
<210> SEQ ID NO 17
<211> LENGTH: 25
<212> TYPE: DNA
<213> ORGANISM: Artificial
<220> FEATURE:
<223> OTHER INFORMATION: probe

<400> SEQUENCE: 17
gtcttgcaac cgaccagggt cggca                                              25

<210> SEQ ID NO 18
<211> LENGTH: 25
<212> TYPE: DNA
<213> ORGANISM: Artificial
<220> FEATURE:
<223> OTHER INFORMATION: probe

<400> SEQUENCE: 18
ccaccagagc ccatgccttg ttcat                                              25

<210> SEQ ID NO 19
<211> LENGTH: 26
<212> TYPE: DNA
<213> ORGANISM: Artificial
<220> FEATURE:
<223> OTHER INFORMATION: probe

<400> SEQUENCE: 19
atgcagaaag accaaagcat acatat                                             26

<210> SEQ ID NO 20
<211> LENGTH: 25
<212> TYPE: DNA
<213> ORGANISM: Artificial
<220> FEATURE:
<223> OTHER INFORMATION: probe

<400> SEQUENCE: 20
cggcactact gctgacaaaa ttgct                                              25

<210> SEQ ID NO 21
<211> LENGTH: 21
<212> TYPE: DNA
<213> ORGANISM: Artificial
<220> FEATURE:
<223> OTHER INFORMATION: primer

<400> SEQUENCE: 21
caatctagca gatgaagcag g                                                  21

<210> SEQ ID NO 22
<211> LENGTH: 23
<212> TYPE: DNA
<213> ORGANISM: Artificial
<220> FEATURE:
<223> OTHER INFORMATION: primer

<400> SEQUENCE: 22
tcaatactct tgcacattgt gat                                                23

<210> SEQ ID NO 23
<211> LENGTH: 22
<212> TYPE: DNA
<213> ORGANISM: Artificial
<220> FEATURE:
<223> OTHER INFORMATION: primer
```

<400> SEQUENCE: 23
ccgggatggt tagctgtaac ag                                    22

<210> SEQ ID NO 24
<211> LENGTH: 26
<212> TYPE: DNA
<213> ORGANISM: Artificial
<220> FEATURE:
<223> OTHER INFORMATION: primer

<400> SEQUENCE: 24
catggtgttg agaaggaact tgtagt                                26

<210> SEQ ID NO 25
<211> LENGTH: 22
<212> TYPE: DNA
<213> ORGANISM: Artificial
<220> FEATURE:
<223> OTHER INFORMATION: primer

<400> SEQUENCE: 25
cgtcaatcac gtggacaaag ag                                    22

<210> SEQ ID NO 26
<211> LENGTH: 20
<212> TYPE: DNA
<213> ORGANISM: Artificial
<220> FEATURE:
<223> OTHER INFORMATION: primer

<400> SEQUENCE: 26
gaagttccga tcaacttcac                                       20

<210> SEQ ID NO 27
<211> LENGTH: 18
<212> TYPE: DNA
<213> ORGANISM: Artificial
<220> FEATURE:
<223> OTHER INFORMATION: primer

<400> SEQUENCE: 27
acagggatcg gaaatcat                                         18

<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
caaaggcttg cccaaagata                                       20

<210> SEQ ID NO 29
<211> LENGTH: 21
<212> TYPE: DNA
<213> ORGANISM: Artificial
<220> FEATURE:
<223> OTHER INFORMATION: primer

<400> SEQUENCE: 29
gtatgtggaa gttagattgg g                                     21

<210> SEQ ID NO 30
<211> LENGTH: 24

```
<212> TYPE: DNA
<213> ORGANISM: Artificial
<220> FEATURE:
<223> OTHER INFORMATION: primer

<400> SEQUENCE: 30
gagtacatgt cgttaaacct ggtg                                          24

<210> SEQ ID NO 31
<211> LENGTH: 21
<212> TYPE: DNA
<213> ORGANISM: Artificial
<220> FEATURE:
<223> OTHER INFORMATION: primer

<400> SEQUENCE: 31
ggttgtttgg ttggttattc g                                             21

<210> SEQ ID NO 32
<211> LENGTH: 21
<212> TYPE: DNA
<213> ORGANISM: Artificial
<220> FEATURE:
<223> OTHER INFORMATION: primer

<400> SEQUENCE: 32
atacgaagaa accttgctga c                                             21

<210> SEQ ID NO 33
<211> LENGTH: 21
<212> TYPE: DNA
<213> ORGANISM: Artificial
<220> FEATURE:
<223> OTHER INFORMATION: primer

<400> SEQUENCE: 33
taccttcttg tacttacttc c                                             21

<210> SEQ ID NO 34
<211> LENGTH: 21
<212> TYPE: DNA
<213> ORGANISM: Artificial
<220> FEATURE:
<223> OTHER INFORMATION: primer

<400> SEQUENCE: 34
tccacgactc tgtaccactt g                                             21

<210> SEQ ID NO 35
<211> LENGTH: 21
<212> TYPE: DNA
<213> ORGANISM: Artificial
<220> FEATURE:
<223> OTHER INFORMATION: primer

<400> SEQUENCE: 35
agtaccatgt cttggaacgg t                                             21

<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
```
aagctctcct gaagctcttt                                              20

<210> SEQ ID NO 37
<211> LENGTH: 26
<212> TYPE: DNA
<213> ORGANISM: Artificial
<220> FEATURE:
<223> OTHER INFORMATION: primer

<400> SEQUENCE: 37
cgcggacctg cgctacaccc tggacc                                       26

<210> SEQ ID NO 38
<211> LENGTH: 20
<212> TYPE: DNA
<213> ORGANISM: Artificial
<220> FEATURE:
<223> OTHER INFORMATION: primer

<400> SEQUENCE: 38
gaagccgaag aaaagctcaa                                              20

<210> SEQ ID NO 39
<211> LENGTH: 20
<212> TYPE: DNA
<213> ORGANISM: Artificial
<220> FEATURE:
<223> OTHER INFORMATION: primer

<400> SEQUENCE: 39
gatacattct ttggaacgat                                              20

<210> SEQ ID NO 40
<211> LENGTH: 21
<212> TYPE: DNA
<213> ORGANISM: Artificial
<220> FEATURE:
<223> OTHER INFORMATION: primer

<400> SEQUENCE: 40
tacagttgta ccgatgaatg g                                            21

<210> SEQ ID NO 41
<211> LENGTH: 18
<212> TYPE: DNA
<213> ORGANISM: Artificial
<220> FEATURE:
<223> OTHER INFORMATION: tag sequence

<400> SEQUENCE: 41
tagcaggatc cctctaag                                                18

<210> SEQ ID NO 42
<211> LENGTH: 27
<212> TYPE: DNA
<213> ORGANISM: Artificial
<220> FEATURE:
<223> OTHER INFORMATION: T7 RNA polymerase promoter sequence

<400> SEQUENCE: 42
aattctaata cgactcacta tagggag                                      27

<210> SEQ ID NO 43
<211> LENGTH: 23
<212> TYPE: DNA
<213> ORGANISM: Artificial

```
<220> FEATURE:
<223> OTHER INFORMATION: T7 RNA polymerase promoter sequence

<400> SEQUENCE: 43
ctaatacgac tcactatagg gag                                              23

<210> SEQ ID NO 44
<211> LENGTH: 25
<212> TYPE: DNA
<213> ORGANISM: Artificial
<220> FEATURE:
<223> OTHER INFORMATION: probe

<400> SEQUENCE: 44
aacttgtccg cattgccacg gttct                                            25

<210> SEQ ID NO 45
<211> LENGTH: 25
<212> TYPE: DNA
<213> ORGANISM: Artificial
<220> FEATURE:
<223> OTHER INFORMATION: probe

<400> SEQUENCE: 45
tcaagggatt aaatcctgcg aacgt                                            25

<210> SEQ ID NO 46
<211> LENGTH: 25
<212> TYPE: DNA
<213> ORGANISM: Artificial
<220> FEATURE:
<223> OTHER INFORMATION: probe

<400> SEQUENCE: 46
aagaagcagc tataggaaaa gaagt                                            25

<210> SEQ ID NO 47
<211> LENGTH: 25
<212> TYPE: DNA
<213> ORGANISM: Artificial
<220> FEATURE:
<223> OTHER INFORMATION: probe

<400> SEQUENCE: 47
tcgaacaggg cggcatgggc ggcgg                                            25

<210> SEQ ID NO 48
<211> LENGTH: 24
<212> TYPE: DNA
<213> ORGANISM: Artificial
<220> FEATURE:
<223> OTHER INFORMATION: probe

<400> SEQUENCE: 48
tccaggttca ccggggtttc cacc                                             24

<210> SEQ ID NO 49
<211> LENGTH: 25
<212> TYPE: DNA
<213> ORGANISM: Artificial
<220> FEATURE:
<223> OTHER INFORMATION: probe

<400> SEQUENCE: 49
tgtgatagct gtggtggctc tgggg                                            25
```

-continued

<210> SEQ ID NO 50
<211> LENGTH: 25
<212> TYPE: DNA
<213> ORGANISM: Artificial
<220> FEATURE:
<223> OTHER INFORMATION: probe

<400> SEQUENCE: 50
atcttgtgaa acctgttctg gtcaa                                          25

<210> SEQ ID NO 51
<211> LENGTH: 25
<212> TYPE: DNA
<213> ORGANISM: Artificial
<220> FEATURE:
<223> OTHER INFORMATION: probe

<400> SEQUENCE: 51
ggggcgctga tttgcaattt aatgt                                          25

<210> SEQ ID NO 52
<211> LENGTH: 25
<212> TYPE: DNA
<213> ORGANISM: Artificial
<220> FEATURE:
<223> OTHER INFORMATION: probe

<400> SEQUENCE: 52
cagaagcgtg cggcctacga tcagt                                          25

<210> SEQ ID NO 53
<211> LENGTH: 24
<212> TYPE: DNA
<213> ORGANISM: Artificial
<220> FEATURE:
<223> OTHER INFORMATION: probe

<400> SEQUENCE: 53
gctctgcaac gacttgcgga actc                                           24

<210> SEQ ID NO 54
<211> LENGTH: 22
<212> TYPE: DNA
<213> ORGANISM: Artificial
<220> FEATURE:
<223> OTHER INFORMATION: primer

<400> SEQUENCE: 54
agcgtatgaa atcctgactg at                                             22

<210> SEQ ID NO 55
<211> LENGTH: 20
<212> TYPE: DNA
<213> ORGANISM: Artificial
<220> FEATURE:
<223> OTHER INFORMATION: primer

<400> SEQUENCE: 55
gcgaggtgtc gctctgcaac                                                20

<210> SEQ ID NO 56
<211> LENGTH: 20
<212> TYPE: DNA
<213> ORGANISM: Artificial
<220> FEATURE:
<223> OTHER INFORMATION: primer

```
<400> SEQUENCE: 56
caaagatatc gctgaagtcg                                          20

<210> SEQ ID NO 57
<211> LENGTH: 21
<212> TYPE: DNA
<213> ORGANISM: Artificial
<220> FEATURE:
<223> OTHER INFORMATION: primer

<400> SEQUENCE: 57
gatgtgcaag gtggtggtgg a                                        21
```

METHOD FOR DETECTING PNEUMONIA CAUSATIVE BACTERIA USING NUCLEIC ACID CHROMATOGRAPHY

CROSS-REFERENCE TO RELATED APPLICATIONS

This application is a National Stage application of PCT/JP2011/001934, filed Mar. 30, 2011, which claims priority from Japanese patent application nos. JP 2010-083823, filed Mar. 31, 2010, and JP 2010-083836, filed Mar. 31, 2010.

The instant application contains a Sequence Listing which has been submitted in ASCII format via EFS-WEB and is hereby incorporated by reference in its entirety. Said ASCII copy, created on Sep. 26, 2012, is named sequence.txt and is 10 KB.

TECHNICAL FIELD

The present invention relates to a method and a kit for detecting pneumonia causative bacteria. More specifically, the present invention relates to a method and a kit for detecting pneumonia causative bacteria intended for *Streptococcus pneumoniae, Haemophilus influenzae, Mycoplasma pneumoniae, Chlamydophila pneumoniae, Legionella pneumophila, Klebsiella pneumoniae, Pseudomonas aeruginosa, Moraxella catarrhalis*, methicillin-resistant *Staphylococcus aureus* (MRSA), and *Staphylococcus aureus*.

BACKGROUND ART

Pneumonia is currently ranked in the fourth place in the cause-specific death rates of Japanese. This disease is known to often complicate underlying diseases such as cancer and affect an extremely large number of individuals. Culture tests, which have heretofore been performed to search for microbes causative of pneumonia (causative bacteria), allegedly fail to serve as testing methods sufficiently contributing to the selection of treatment, because they require at least a few days and may involve a nearly 1-week additional drug sensitivity test on the cultured causative bacteria. In the case of severe pneumonia requiring hospitalization in intensive care unit (ICU), the accurate and rapid determination of causative bacteria is exceedingly important for the selection of treatment thereof. According to reports, appropriate initial treatment reliably increases the survival rate of pneumonia patients. In fact, however, a technique of identifying causative bacteria as a substitute for the culture tests still remains to be established. Under the circumstances, pneumonia must be treated with causative bacteria unidentified, possibly leading to the emergence of resistant bacteria due to reluctant use of antibiotics based on empirical treatment.

Highly frequently occurring bacterial strains account for nearly 50% of all causative bacteria responsible for pneumonia. Main causative bacteria, also including viruses, are allegedly of approximately 20 to 30 types. Some of these bacteria cannot be cultured by a usual approach. Also in some cases, causative bacteria are difficult to determine even by culture. Particularly, for pneumonia requiring treatment with antibiotics appropriately selected depending on bacterial strains/bacterial volumes, it is very important to simultaneously detect plural types of pneumonia causative bacteria and quantitatively analyze detected signals. Although the optimum therapeutic drug differs depending on the type of causative bacteria, the fact is that medical ethics compels treatment to be started before determination of causative bacteria. The development of an approach capable of rapidly and quantitatively detecting particular bacteria from among a plurality of bacterial strains has been awaited in order to solve these problems.

Proposed is, for example, a method for simultaneously detecting four types of respiratory infection causative bacteria using primers respectively derived from a lytA gene encoding *Streptococcus pneumoniae* autolysin (LytA), a gene encoding *Haemophilus influenza* 16S rRNA, a gene encoding *Streptococcus pyogenes* 16S rRNA, and a gene encoding *Mycoplasma pneumoniae* 16S rRNA or a primer set thereof in combination with primers derived from a gene encoding *Legionella pneumophila* 16S rRNA and a mip gene encoding the *Legionella pneumophila* causative factor MIP protein (see e.g., patent document 1).

Also proposed are a primer set and a probe oligonucleotide set specific for ten types of respiratory disease-related bacteria consisting of a primer set comprising first oligonucleotides and second oligonucleotides and specifically amplifying target sequences present in *Bordetella pertussis, Chlamydophila pneumoniae, Haemophilus influenza, Mycoplasma pneumoniae, Klebsiella pneumoniae, Legionella pneumoniae, Moraxella catarrhalis, Pseudomonas aeruginosa, Staphylococcus aureus*, and *Streptococcus pneumoniae* with nucleic acids separated from a bacterium-containing sample as templates, and probes specifically detecting target nucleic acids present in the bacteria (see e.g., patent documents 2 and 3).

Also proposed are: a nucleic acid primer set capable of simultaneously amplifying target sequences of five or more types of respiratory disease causative viruses, wherein each primer is selected from oligonucleotides comprising a fragment of ten or more consecutive bases; and probe oligonucleotides for detecting one or more of measles virus, enterovirus, rhinovirus, SARS-related coronavirus (SARS-coV), varicella-zoster virus (VZV), adenovirus, human parainfluenza virus 1 (HPIV1), human parainfluenza virus 2 (HPIV2), human parainfluenza virus 3 (HPIV3), influenza virus A (IVA), influenza virus B (IVB), respiratory syncytial virus A (RSVA), and respiratory syncytial virus B (RSVB), comprising one or more oligonucleotides of 10 bp to 100 bp in length selected from the group consisting of oligonucleotides comprising a fragment of ten or more consecutive bases and oligonucleotides complementary thereto. It is disclosed that this approach comprises the steps of: obtaining nucleic acids from a sample; amplifying the nucleic acids using the nucleic acid primer set; and detecting the amplification products. It is also disclosed that: the step of obtaining nucleic acids from a sample comprises the steps of separating RNAs from the sample and obtaining cDNAs from the separated RNAs, wherein the step of obtaining cDNAs is performed using, for example, reverse transcriptase; reverse transcriptase reaction using the reverse transcriptase may be based on RT-PCR; and the amplification step may be performed by PCR (see e.g., patent document 4).

Further proposed is a simple, highly sensitive norovirus detection method for specifically amplifying genes broadly classified into norovirus gene groups genogroup I (GI) and genogroup II (GII) present in trace amounts in a sample, the method consisting of steps including the steps of: performing an NASBA method capable of amplifying nucleic acids at a predetermined temperature on RNAs extracted from the sample to obtain complementary single-stranded nucleic acids; and further amplifying the nucleic acids by an RT-LAMP method capable of amplifying, at a predetermined temperature, the amplification products obtained by the NASBA method (see e.g., patent document 5).

The present inventors have proposed a primer set for use in the detection of plural types of pneumonia causative bacteria, the primer set allowing simultaneous detection of *Streptococcus pneumoniae*, *Haemophilus influenza*, *Mycoplasma pneumoniae*, and *Chlamydophila pneumoniae* by usual PCR as well as multiplex PCR, real-time PCR, RT-PCR, etc. (see e.g., patent document 6), a method for detecting or quantifying a target RNA, comprising preparing, from a bacterium-specific RNA strand in 16S rRNA, a liquid-phase universal primer in which an RNA polymerase promoter sequence is added via a tag sequence to the 5' end of a DNA sequence corresponding to a specific sequence of the target RNA (see e.g., patent document 7), and a method for detecting pathogenic microbes, wherein the pathogenic microbes are two or more species selected from one or more bacteria selected from bacteria of the genera *Staphylococcus*, *Streptococcus*, *Klebsiella*, *Escherichia*, *Mycobacterium*, *Legionella*, *Vibrio*, *Bacillus*, *Neisseria*, *Campylobacter*, *Chlamydia*, *Chlamydophila*, *Mycoplasma*, *Listeria*, *Salmonella*, and *Yersinia*, the method comprising a polymerase chain reaction step of carrying out polymerase chain reaction using at least one type of first primer set having a tag sequence and a nucleotide sequence selectively annealing to a target nucleic acid on the DnaJ gene carried by the pathogenic microbes and at least one type of second primer set having a tag sequence substantially identical to the tag sequence of the first primer set, and a step of detecting amplification products comprising the target nucleic acid (see e.g., patent document 8).

The present inventors have also already developed a method for specifically detecting or quantifying a target nucleic acid in a sample, the method comprising the steps of: amplifying the target nucleic acid arbitrarily extracted from the sample using hapten- or peptide-unbound primers to obtain single-stranded nucleic acid; hybridizing the amplification product with a membrane bound-first oligonucleotide probe complementary to the amplification product and a complementary second oligonucleotide probe labeled with a colored high molecular carrier, followed by a detection; and evaluating the detection image by visual judgment, and have established a method comprising performing NASBA amplification reaction with total RNA extracted from, for example, a cultured strain of methicillin-resistant *Staphylococcus aureus* (MRSA), as a template and detecting the amplification product using a nucleic acid chromatography strip (see e.g., patent document 9).

There is also a report on a reagent (Swiftgene Norovirus GI/GII "Kainos") for detecting two genotypes of norovirus genes by the NASBA method and nucleic acid chromatography in combination. Judgment using this reagent is based on broad classification into genetically diverse GI type to which 15 or more genotypes belongs and GII type to which 18 or more genotypes belong, and is less than precise for identifying pneumonia causative bacteria.

PRIOR ART DOCUMENTS

Patent Documents

Patent document 1: Japanese unexamined Patent Application Publication No. 2005-110545
Patent document 2: Japanese unexamined Patent Application Publication No. 2006-174837
Patent document 3: Japanese Patent No. 4235645
Patent document 4: Japanese unexamined Patent Application Publication No. 2006-180878
Patent document 5: Japanese unexamined Patent Application Publication No. 2009-240207
Patent document 6: Japanese unexamined Patent Application Publication No. 2009-39046
Patent document 7: International Publication No. WO 2009/057330
Patent document 8: International Publication No. WO 2008/041354
Patent document 9: Japanese Patent No. 4268944

SUMMARY OF THE INVENTION

Object to be Solved by the Invention

An object of the present invention is to provide a method for accurately and rapidly detecting *Streptococcus pneumoniae*, *Haemophilus influenzae*, *Mycoplasma pneumoniae*, *Chlamydophila pneumoniae*, *Legionella pneumophila*, *Klebsiella pneumoniae*, *Pseudomonas aeruginosa*, *Moraxella catarrhalis*, methicillin-resistant *Staphylococcus aureus* (MRSA), *Staphylococcus aureus* (hereinafter, these individual bacteria are also referred to as "targeting pneumonia bacteria" or simply as "pneumonia bacteria", or collectively referred to as "ten types of targeting pneumonia bacteria") in the diagnosis of pneumonia patients, and a detection kit for use therein.

Means to Solve the Object

The present inventors have studied a method for enhancing the detection precision of pneumonia causative bacteria in order to achieve clinical practice. On the basis of the findings that the DnaJ gene has about 10 times polymorphisms of the 16S rRNA sequence, the present inventors have focused on various pneumonia bacterium-specific gene regions including the DnaJ region, and designed, for ten types of targeting pneumonia bacteria, a set of primer pairs directed to their respective target regions contained in the DnaJ gene, etc., of the ten types of pneumonia causative bacteria. Consequently, it has been found that plural types of pneumonia causative bacteria can be detected with high precision by amplifying gene products by an NASBA method using the set of primer pairs and qualitatively or quantitatively detecting the target nucleic acids as the amplification products. The present inventors have further designed, for the ten types of targeting pneumonia bacteria, a set of pneumonia bacterium-specific probe pairs such that the probe pairs hybridize with the amplification products via sequences in the respective target regions differing from the sequences hybridized by the set of primer pairs. Consequently, it has been found that plural types (up to ten types) of targeting pneumonia bacteria can be detected with high precision in one operation by performing nucleic acid chromatography using the set of probe pairs. The present invention has been completed on the basis of these findings.

Specifically, the present invention relates to: (1) a method for detecting pneumonia causative bacteria targeting at least three types of pneumonia bacteria selected from *Streptococcus pneumoniae*, *Haemophilus influenzae*, *Mycoplasma pneumoniae*, *Chlamydophila pneumoniae*, *Legionella pneumophila*, *Klebsiella pneumoniae*, *Pseudomonas aeruginosa*, *Moraxella catarrhalis*, methicillin-resistant *Staphylococcus aureus* (MRSA), and *Staphylococcus aureus*, the method comprising the following steps: 1) step (a) of amplifying a single-stranded nucleic acid using a primer from pneumonia bacterium-specific target nucleic acids arbitrarily extracted from a sample; 2) step (b) of preparing at least three types of probe pairs differing by the pneumonia bacteria, wherein the probe pairs are selected from a nucleotide sequence complementary to an amplification product; 3) step (c) of binding a first probe for the at least three types of pneumonia bacteria to a labeled high molecular carrier to prepare a first probe-bound labeled high molecular carrier; 4) step (d) of immobilizing a second probe for the at least three types of pneumonia bacteria paired with the first probe, to a predetermined positions distinguishable for each of the pneumonia bacteria to prepare a second probe-carrying developing support; 5) step (e) of hybridizing the amplification product to the second probe carried by the developing support and the first probe bound with the labeled high molecular carrier, followed by a detection; and 6) step (f) of evaluating and assessing the detection image; (2) the detection method according to (1), wherein the primer is at least three types of primer pairs differing by the pneumonia bacteria, wherein the primer pairs are selected from a forward primer consisting of the nucleotide sequence represented by SEQ ID NO: 21 and a reverse primer consisting of the nucleotide sequence represented by SEQ ID NO: 31 and an RNA polymerase promoter sequence added to the 5' end thereof; a forward primer consisting of the nucleotide sequence represented by SEQ ID NO: 22 and a reverse primer consisting of the nucleotide sequence represented by SEQ ID NO: 32 and an RNA polymerase promoter sequence added to the 5' end thereof; a forward primer consisting of the nucleotide sequence represented by SEQ ID NO: 23 and a reverse primer consisting of the nucleotide sequence represented by SEQ ID NO: 33 and an RNA polymerase promoter sequence added to the 5' end thereof; a forward primer consisting of the nucleotide sequence represented by SEQ ID NO: 24 and a reverse primer consisting of the nucleotide sequence represented by SEQ ID NO: 34 and an RNA polymerase promoter sequence added to the 5' end thereof; a forward primer consisting of the nucleotide sequence represented by SEQ ID NO: 25 and a reverse primer consisting of the nucleotide sequence represented by SEQ ID NO: 35 and an RNA polymerase promoter sequence added to the 5' end thereof; a forward primer consisting of the nucleotide sequence represented by SEQ ID NO: 26 and a reverse primer consisting of the nucleotide sequence represented by SEQ ID NO: 36 and an RNA polymerase promoter sequence added to the 5' end thereof; a forward primer consisting of the nucleotide sequence represented by SEQ ID NO: 27 and a reverse primer consisting of the nucleotide sequence represented by SEQ ID NO: 37 and an RNA polymerase promoter sequence added to the 5' end thereof; a forward primer consisting of the nucleotide sequence represented by SEQ ID NO: 28 and a reverse primer consisting of the nucleotide sequence represented by SEQ ID NO: 38 and an RNA polymerase promoter sequence added to the 5' end thereof; a forward primer consisting of the nucleotide sequence represented by SEQ ID NO: 29 and a reverse primer consisting of the nucleotide sequence represented by SEQ ID NO: 39 and an RNA polymerase promoter sequence added to the 5' end thereof; and a forward primer consisting of the nucleotide sequence represented by SEQ ID NO: 30 and a reverse primer consisting of the nucleotide sequence represented by SEQ ID NO: 40 and an RNA polymerase promoter sequence added to the 5' end thereof; and (3) the detection method according to (1) or (2), wherein the first probe for the at least three types of pneumonia bacteria consists of at least three types of DNAs selected from the nucleotide sequences represented by SEQ ID NOs: 1 to 10, and the second probe for the at least three types of pneumonia bacteria to be paired with the first probe is at least three types of DNAs selected from the nucleotide sequences represented by SEQ ID NOs: 11 to 20.

The present invention also relates to: (4) a kit for detecting pneumonia causative bacteria targeting at least three types of pneumonia bacteria selected from *Streptococcus pneumoniae*, *Haemophilus influenzae*, *Mycoplasma pneumoniae*, *Chlamydophila pneumoniae*, *Legionella pneumophila*, *Klebsiella pneumoniae*, *Pseudomonas aeruginosa*, *Moraxella catarrhalis*, methicillin-resistant *Staphylococcus aureus* (MRSA), and *Staphylococcus aureus*, the kit comprising at least three types of primer pairs differing by the pneumonia bacteria, which are capable of amplifying a pneumonia bacterium-specific target nucleic acid arbitrarily extracted from a sample, wherein the primer pairs are selected from a forward primer consisting of the nucleotide sequence represented by SEQ ID NO: 21 and a reverse primer consisting of the nucleotide sequence represented by SEQ ID NO: 31 and an RNA polymerase promoter sequence added to the 5' end thereof; a forward primer consisting of the nucleotide sequence represented by SEQ ID NO: 22 and a reverse primer consisting of the nucleotide sequence represented by SEQ ID NO: 32 and an RNA polymerase promoter sequence added to the 5' end thereof; a forward primer consisting of the nucleotide sequence represented by SEQ ID NO: 23 and a reverse primer consisting of the nucleotide sequence represented by SEQ ID NO: 33 and an RNA polymerase promoter sequence added to the 5' end thereof; a forward primer consisting of the nucleotide sequence represented by SEQ ID NO: 24 and a reverse primer consisting of the nucleotide sequence represented by SEQ ID NO: 34 and an RNA polymerase promoter sequence added to the 5' end thereof; a forward primer consisting of the nucleotide sequence represented by SEQ ID NO: 25 and a reverse primer consisting of the nucleotide sequence represented by SEQ ID NO: 35 and an RNA polymerase promoter sequence added to the 5' end thereof; a forward primer consisting of the nucleotide sequence represented by SEQ ID NO: 26 and a reverse primer consisting of the nucleotide sequence represented by SEQ ID NO: 36 and an RNA polymerase promoter sequence added to the 5' end thereof; a forward primer consisting of the nucleotide sequence represented by SEQ ID NO: 27 and a reverse primer consisting of the nucleotide sequence represented by SEQ ID NO: 37 and an RNA polymerase promoter sequence added to the 5' end thereof; a forward primer consisting of the nucleotide sequence represented by SEQ ID NO: 28 and a reverse primer consisting of the nucleotide sequence represented by SEQ ID NO: 38 and an RNA polymerase promoter sequence added to the 5' end thereof; a forward primer consisting of the nucleotide sequence represented by SEQ ID NO: 29 and a reverse primer consisting of the nucleotide sequence represented by SEQ ID NO: 39 and an RNA polymerase promoter sequence added to the 5' end thereof; and a forward primer consisting of the nucleotide sequence represented by SEQ ID NO: 30 and a reverse primer consisting of the nucleotide sequence represented by SEQ ID NO: 40 and an RNA polymerase promoter sequence added to the 5' end thereof; (5) the kit according to (4), further comprising 1) a first probe-bound labeled high molecular carrier in which a first probe for the at least three types of pneumonia bacteria differing by the pneumonia bacteria is bound to a labeled high molecular carrier, wherein the first probe is selected from a nucleotide sequence complementary to an amplification product; and 2) a second probe-carrying developing support in which a second probe for the at least three types of pneumonia bacteria to be paired with the first probe is immobilized at a predetermined position distinguishable for each of the pneumonia bacteria; and (6) the kit according to (5), wherein the first probe for the at least three types of pneumonia bacteria consists of at least three types of DNAs selected from the nucleotide sequences represented by SEQ ID NOs: 1 to 10, and the second probe for the at least three types of pneumonia bacteria to be paired with the first probe is at least three types of DNAs selected from the nucleotide sequences represented by SEQ ID NOs: 11 to 20.

Effect of the Invention

The present invention has enabled pneumonia causative bacteria to be accurately and rapidly identified by a convenient method in the diagnosis of pneumonia patients.

BRIEF DESCRIPTION OF DRAWINGS

FIG. 9 is a diagram showing results of verifying the presence or absence of nonspecific reaction of each primer pair with a bacterium other than its target after multiplexing of ten primer pairs used in the present invention.

FIG. 16 is a diagram showing results of verifying the presence or absence of nonspecific reaction of each probe with a bacterium other than its target.

MODE OF CARRYING OUT THE INVENTION

Figure 1:
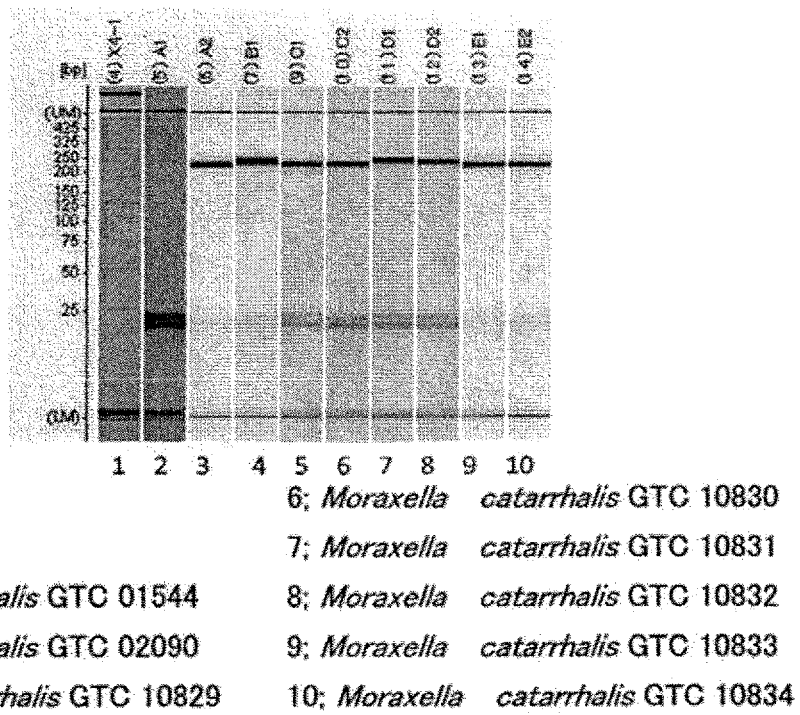
FIG. 1 is a diagram showing data from verification using primer pairs directed to eight *Moraxella catarrhalis* strains.
Figure 2:
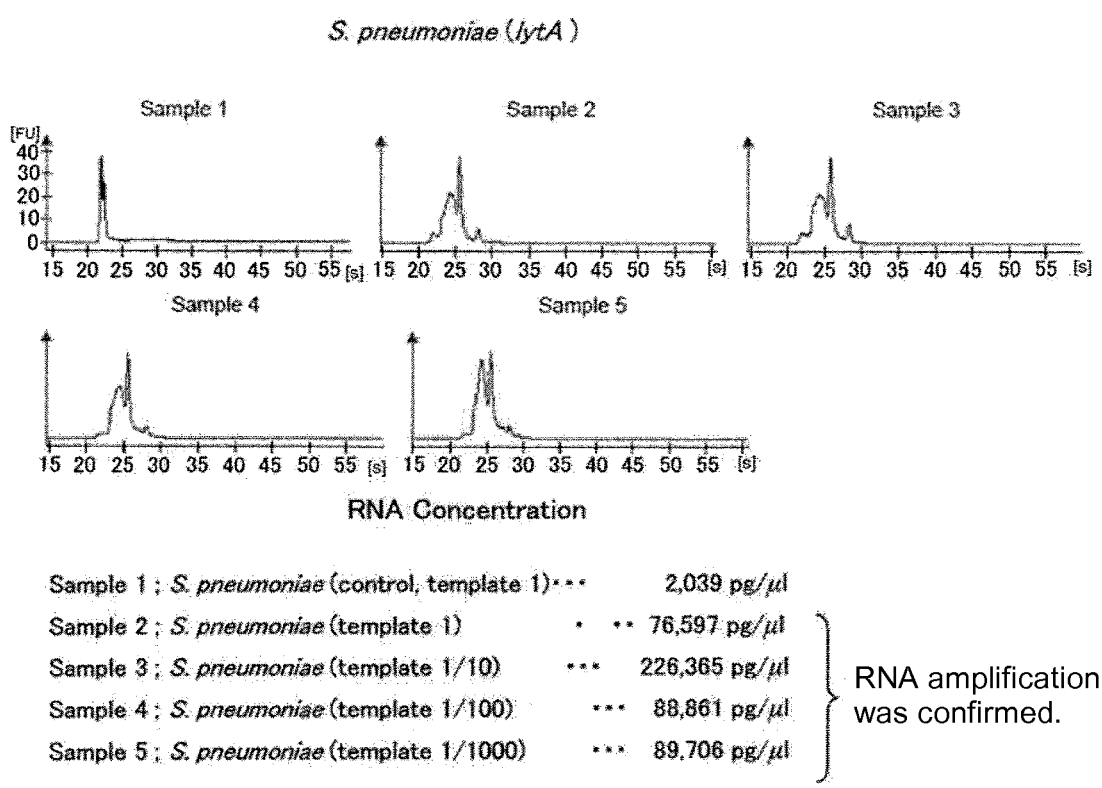
FIG. 2 is a diagram showing data from the RNA amplification of a target gene in *Streptococcus pneumoniae* by the NASBA method with a pneumonia bacterium-specific primer pair used in the present invention.
Figure 3:
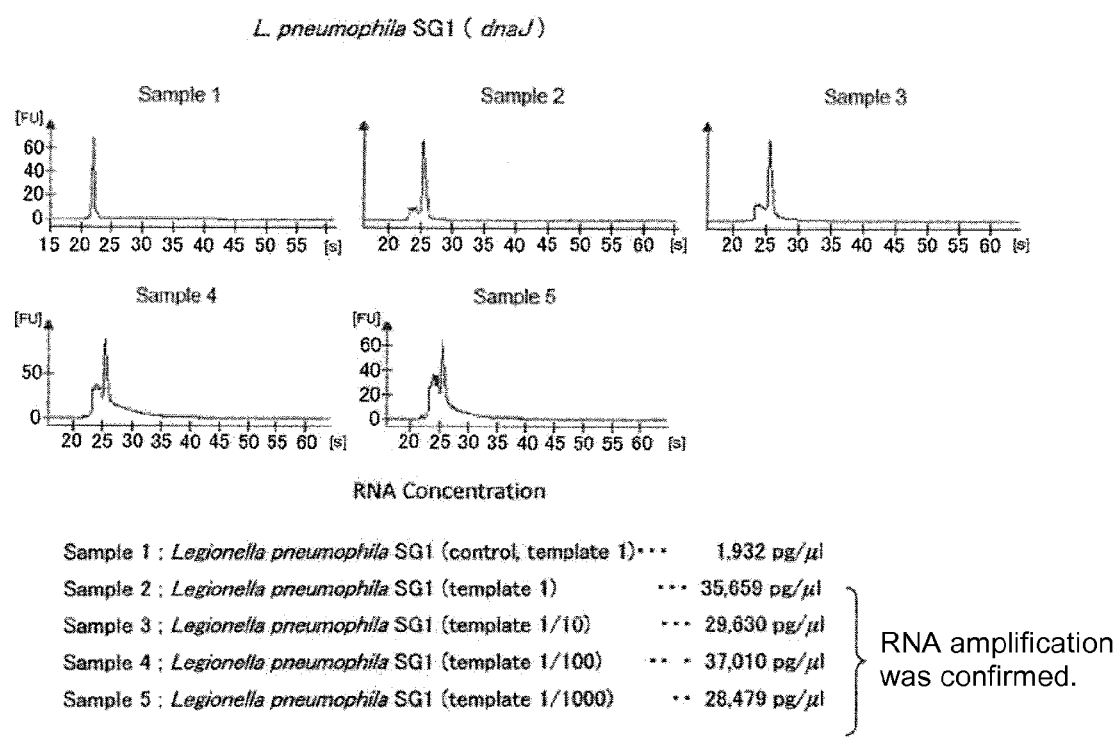
FIG. 3 is a diagram showing data from the RNA amplification of a target gene in *Legionella pneumophila* by the NASBA method with a pneumonia bacterium-specific primer pair used in the present invention.
Figure 4:
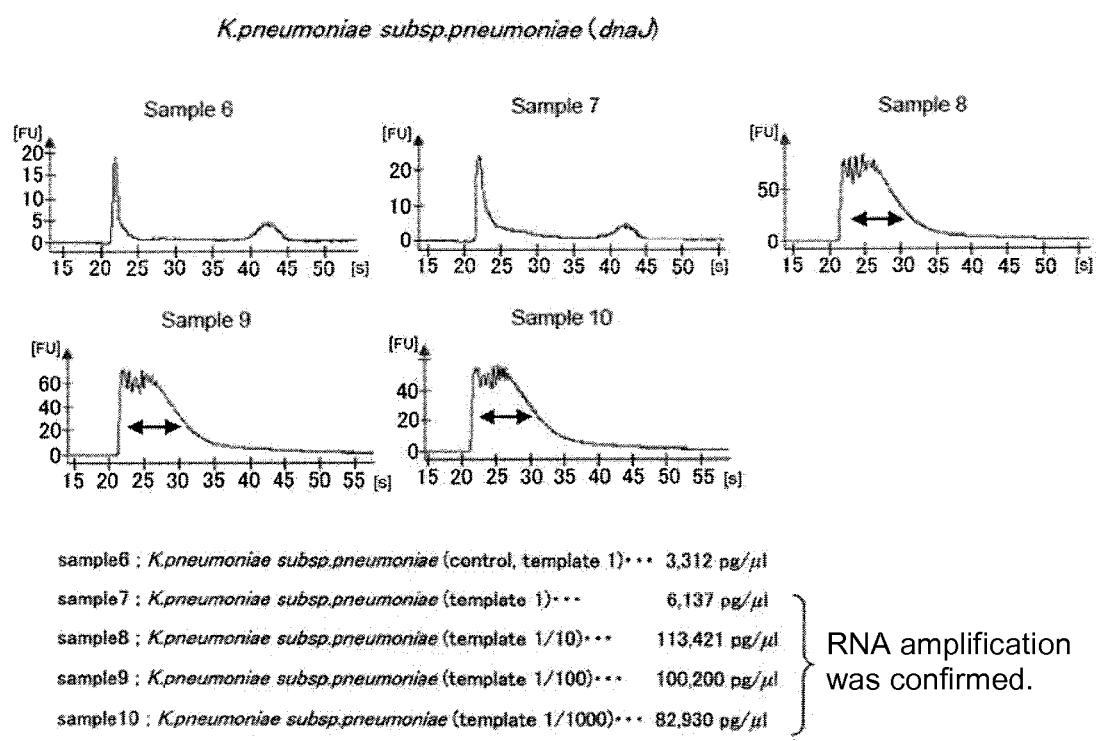
FIG. 4 is a diagram showing data from the RNA amplification of a target gene in *Klebsiella pneumoniae* by the NASBA method with a pneumonia bacterium-specific primer pair used in the present invention.
Figure 5:
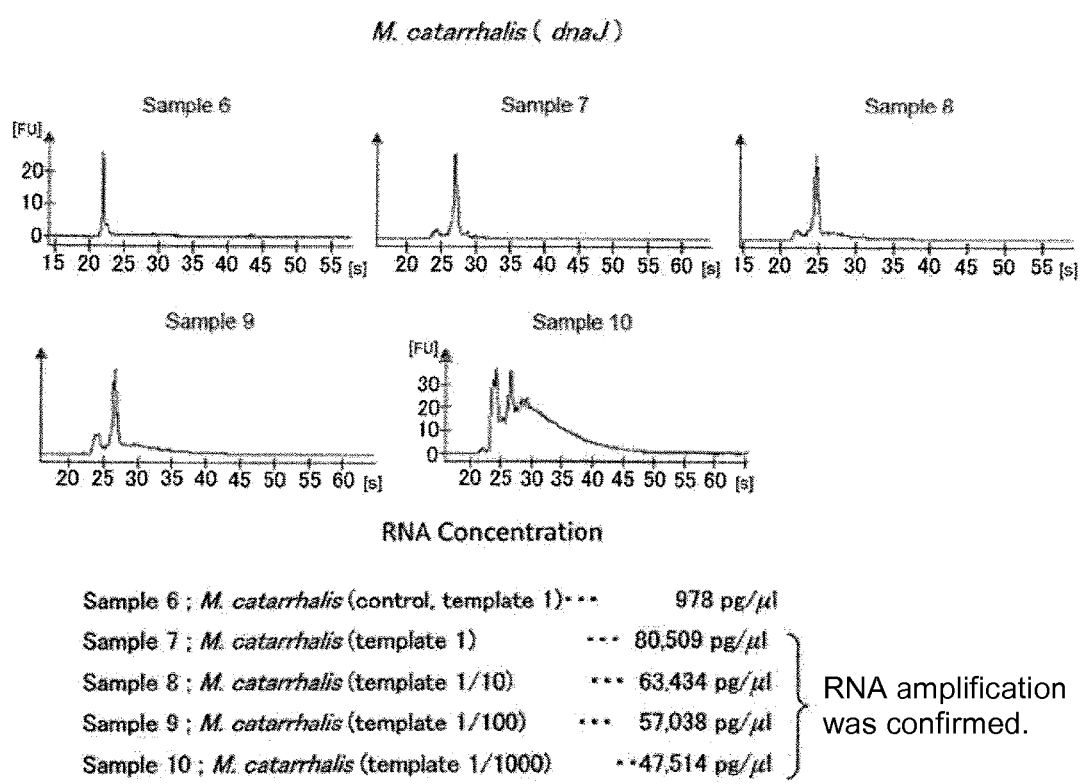
FIG. 5 is a diagram showing data from the RNA amplification of a target gene in *Moraxella catarrhalis* by the NASBA method with a pneumonia bacterium-specific primer pair used in the present invention.
Figure 6:
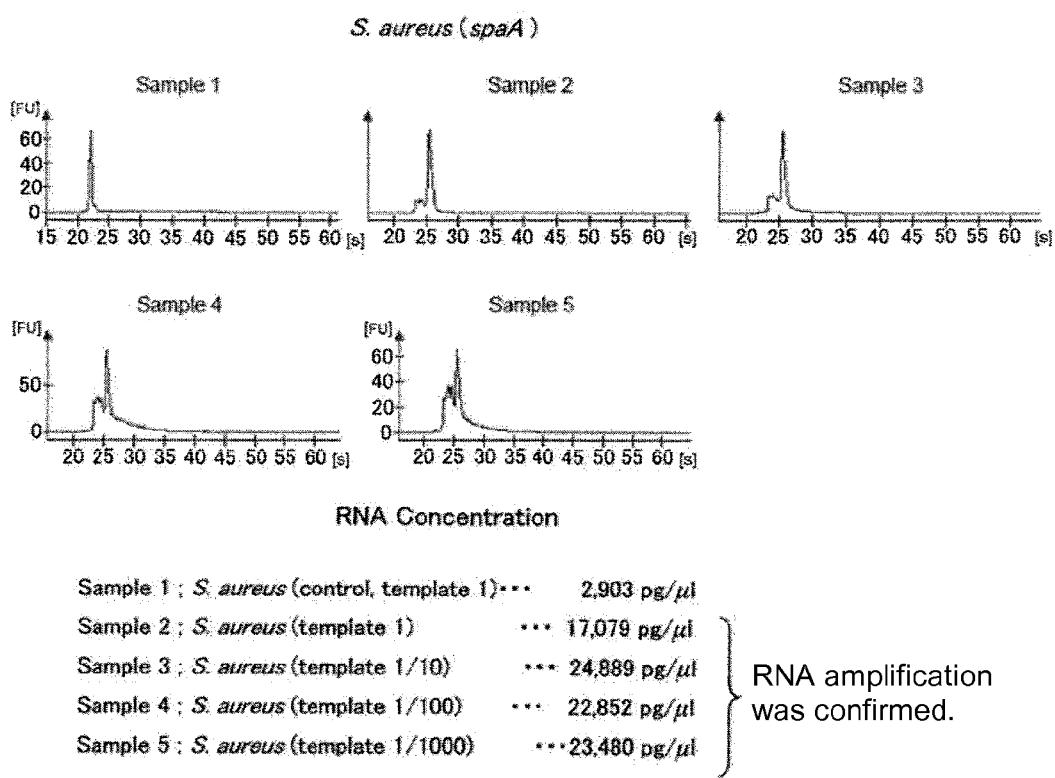
FIG. 6 is a diagram showing data from the RNA amplification of a target gene in *Staphylococcus aureus* by the NASBA method with a pneumonia bacterium-specific primer pair used in the present invention.
Figure 7:
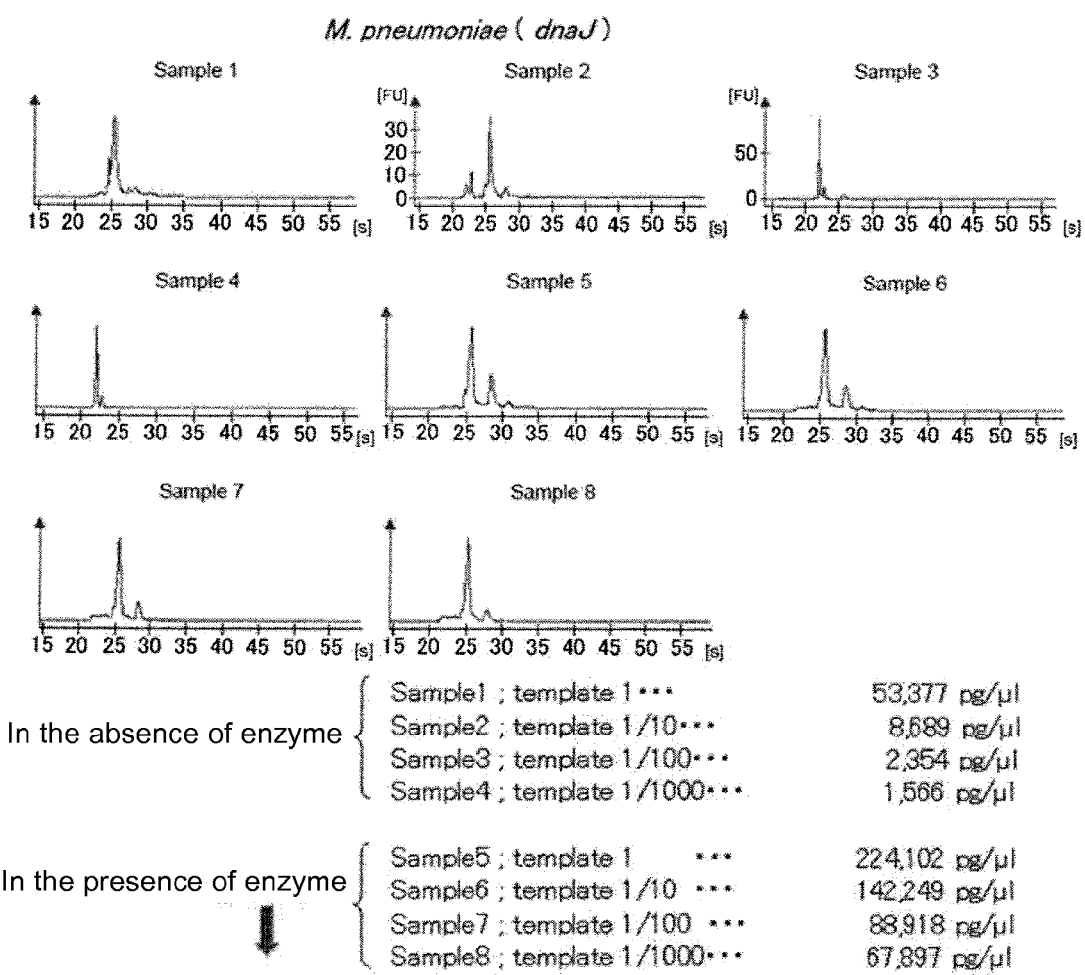
FIG. 7 is a diagram showing data from the RNA amplification of a target gene in *Mycoplasma pneumoniae* by the NASBA method with a pneumonia bacterium-specific primer pair used in the present invention.
Figure 8:
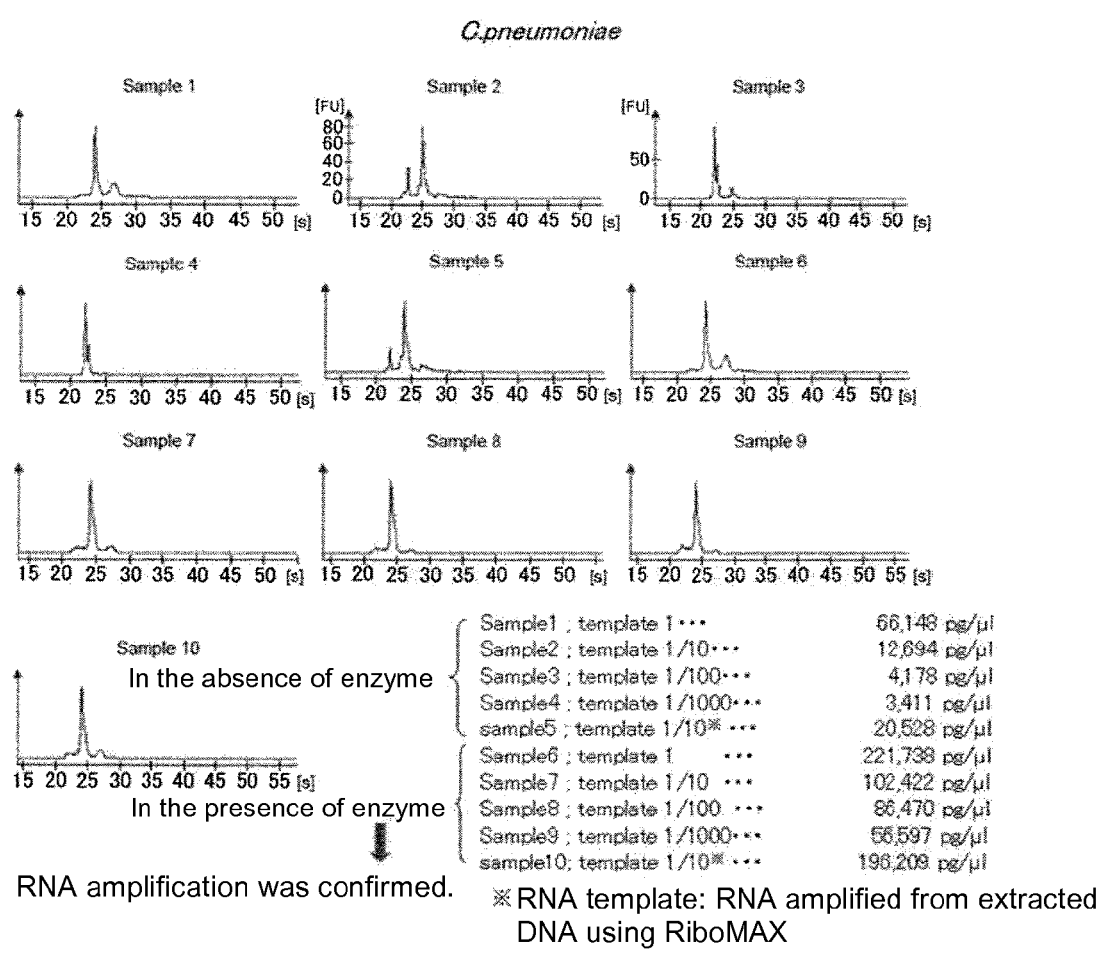
FIG. 8 is a diagram showing data from the RNA amplification of a target gene in *Chlamydophila pneumoniae* by the NASBA method with a pneumonia bacterium-specific primer pair used in the present invention.

The method for detecting pneumonia causative bacteria of the present invention is not particularly limited as long as the detection method is targeting at least three types of pneumonia bacteria selected from ten types of targeting pneumonia bacteria, the method comprising: 1) step (a) of amplifying a single-stranded nucleic acid using primers from a pneumonia bacterium-specific target nucleic acid arbitrarily extracted from a sample; 2) step (b) of preparing at least three types of probe pairs differing by the pneumonia bacteria, wherein the probe pairs are selected from the nucleotide sequences represented by SEQ ID NOs: 1 to 20 complementary to an amplification product; 3) step (c) of binding a first probe for the at least three types of pneumonia bacteria to a labeled high molecular carrier to prepare a first probe-bound labeled high molecular carrier, wherein the first probe for the at least three types of pneumonia bacteria is selected from the nucleotide sequences represented by SEQ ID NOs: 1 to 10; 4) step (d) of immobilizing a second probe for the at least three types of pneumonia bacteria paired with the first probe, to a predetermined position distinguishable for each of the pneumonia bacteria to prepare a solid-phase second probe-carrying developing support, wherein the second probe for the at least three types of pneumonia bacteria to be paired with the first probe is selected from the nucleotide sequences represented by SEQ ID NOs: 11 to 20; 5) step (e) of hybridizing the amplification product with the solid-phase second probe carried by the developing support and the first probe bound to the labeled high molecular carrier, followed by a detection; and 6) step (f) of evaluating and assessing the detection image. For the detection method of the present invention, it is preferred to detect at least five types, i.e., five to ten types of targeting pneumonia bacteria.

Another detection method that can be used as the method for detecting pneumonia causative bacteria of the present invention is intended for at least three types of pneumonia causative bacteria selected from ten types of targeting pneumonia causative bacteria, the method comprising: 1) step (a') of preparing at least three types of primer pairs differing by the pneumonia bacteria, which are capable of amplifying pneumonia bacterium-specific target nucleic acids arbitrarily extracted from a sample, wherein the primer pairs are selected from a forward primer consisting of the nucleotide sequence represented by SEQ ID NO: 21 and a reverse primer consisting of the nucleotide sequence represented by SEQ ID NO: 31 and an RNA polymerase promoter sequence added to the 5' end thereof; a forward primer consisting of the nucleotide sequence represented by SEQ ID NO: 22 and a reverse primer consisting of the nucleotide sequence represented by SEQ ID NO: 32 and an RNA polymerase promoter sequence added to the 5' end thereof; a forward primer consisting of the nucleotide sequence represented by SEQ ID NO: 23 and a reverse primer consisting of the nucleotide sequence represented by SEQ ID NO: 33 and an RNA polymerase promoter sequence added to the 5' end thereof; a forward primer consisting of the nucleotide sequence represented by SEQ ID NO: 24 and a reverse primer consisting of the nucleotide sequence represented by SEQ ID NO: 34 and an RNA polymerase promoter sequence added to the 5' end thereof; a forward primer consisting of the nucleotide sequence represented by SEQ ID NO: 25 and a reverse primer consisting of the nucleotide sequence represented by SEQ ID NO: 35 and an RNA polymerase promoter sequence added to the 5' end thereof; a forward primer consisting of the nucleotide sequence represented by SEQ ID NO: 26 and a reverse primer consisting of the nucleotide sequence represented by SEQ ID NO: 36 and an RNA polymerase promoter sequence added to the 5' end thereof; a forward primer consisting of the nucleotide sequence represented by SEQ ID NO: 27 and a reverse primer consisting of the nucleotide sequence represented by SEQ ID NO: 37 and an RNA polymerase promoter sequence added to the 5' end thereof; a forward primer consisting of the nucleotide sequence represented by SEQ ID NO: 28 and a reverse primer consisting of the nucleotide sequence represented by SEQ ID NO: 38 and an RNA polymerase promoter sequence added to the 5' end thereof; a forward primer consisting of the nucleotide sequence represented by SEQ ID NO: 29 and a reverse primer consisting of the nucleotide sequence represented by SEQ ID NO: 39 and an RNA polymerase promoter sequence added to the 5' end thereof; and a forward primer consisting of the nucleotide sequence represented by SEQ ID NO: 30 and a reverse primer consisting of the nucleotide sequence represented by SEQ ID NO: 40 and an RNA polymerase promoter sequence added to the 5' end thereof; 2) step (b') of contacting at least three types of chimeric primer pairs with a test sample possibly containing the nucleic acids of the targeting pneumonia bacteria to amplify gene products by an RNA amplification method; and 3) step (c') of qualitatively or quantitatively detecting the target nucleic acids as the amplification products. For this method, it is preferred to detect at least five types, i.e., five to ten types of targeting pneumonia bacteria.

Examples of three types of the targeting pneumonia bacteria can include 120 different combinations of three types of pneumonia bacteria consisting of, for example, combinations of three types such as: *Streptococcus pneumoniae, Haemophilus influenzae*, and *Mycoplasma pneumoniae; Streptococcus pneumoniae, Haemophilus influenzae*, and *Legionella pneumophila*; and *Streptococcus pneumoniae, Haemophilus influenzae*, and *Chlamydophila pneumoniae* from among *Streptococcus pneumoniae, Haemophilus influenzae, Mycoplasma pneumoniae, Legionella pneumophila*, and *Chlamydophila pneumoniae* often detected in outpatients (hereinafter, also referred to as "targeting pneumonia bacteria for outpatients"), combinations of three types such as: *Pseudomonas aeruginosa, Klebsiella pneumoniae*, and *Staphylococcus aureus; Klebsiella pneumoniae, Staphylococcus aureus*, and MRSA; *Pseudomonas aeruginosa*, MRSA, and *Moraxella catarrhalis*; and *Staphylococcus aureus*, MRSA, and *Moraxella catarrhalis* from among *Pseudomonas aeruginosa, Klebsiella pneumoniae, Staphylococcus aureus*, MRSA, and *Moraxella catarrhalis* often detected in hospitalized patients due to hospital-acquired infection (hereinafter, also referred to as "targeting pneumonia bacteria for hospitalized patients"), and other combinations of three types such as: *Streptococcus pneumoniae, Haemophilus influenzae*, and MRSA; and *Streptococcus pneumoniae, Haemophilus influenzae*, and *Pseudomonas aeruginosa*.

Examples of four types of the targeting pneumonia bacteria can include 210 different combinations of four types of pneumonia bacteria consisting of, for example, combinations of four types such as: *Streptococcus pneumoniae, Haemophilus influenzae, Mycoplasma pneumoniae*, and *Legionella pneumophila; Streptococcus pneumoniae, Haemophilus influenzae, Mycoplasma pneumoniae*, and *Chlamydophila pneumoniae; Streptococcus pneumoniae, Haemophilus influenzae, Legionella pneumophila*, and *Chlamydophila pneumoniae; Streptococcus pneumoniae, Mycoplasma pneumoniae, Legionella pneumophila*, and *Chlamydophila pneumoniae*; and *Haemophilus influenzae, Mycoplasma pneumoniae, Legionella pneumophila*, and *Chlamydophila pneumoniae* from among the targeting pneumonia bacteria for outpatients, combinations of four types such as; *Pseudomonas aeruginosa, Klebsiella pneumoniae, Staphylococcus aureus*, and MRSA; *Pseudomonas aeruginosa, Klebsiella pneumoniae, Staphylococcus aureus*, and *Moraxella catarrhalis; Pseudomonas aeruginosa, Klebsiella pneumoniae*, MRSA, and *Moraxella catarrhalis; Pseudomonas aeruginosa, Staphylococcus aureus*, MRSA, and *Moraxella catarrhalis*; and *Klebsiella pneumoniae, Staphylococcus aureus*, MRSA, and *Moraxella catarrhalis* from among the targeting pneumonia bacteria for hospitalized patients, and other combinations of four types such as: *Streptococcus pneumoniae, Haemophilus influenzae, Mycoplasma pneumoniae*, and MRSA; and *Streptococcus pneumoniae, Haemophilus influenzae, Pseudomonas aeruginosa*, and MRSA.

Examples of five types of the targeting pneumonia bacteria can include 252 different combinations of five types of pneumonia bacteria consisting of, for example, those five types of targeting pneumonia bacteria for outpatients and those five types of targeting pneumonia bacteria for hospitalized patients as well as *Streptococcus pneumoniae, Haemophilus influenzae, Mycoplasma pneumoniae, Legionella pneumophila*, and MRSA; *Streptococcus pneumoniae, Haemophilus influenzae, Mycoplasma pneumoniae, Chlamydophila pneumoniae*, and MRSA; *Streptococcus pneumoniae, Haemophilus influenzae, Mycoplasma pneumoniae, Chlamydophila pneumoniae*, and *Moraxella catarrhalis; Streptococcus pneumoniae, Haemophilus influenzae, Mycoplasma pneumoniae*, MRSA, and *Staphylococcus aureus; Streptococcus pneumoniae, Haemophilus influenzae, Mycoplasma pneumoniae, Pseudomonas aeruginosa*, and *Chlamydophila pneumoniae*; and *Streptococcus pneumoniae, Haemophilus influenzae, Mycoplasma pneumoniae*, MRSA, and *Moraxella catarrhalis*.

Examples of six types of the targeting pneumonia bacteria can include 210 different combinations of six types of pneumonia bacteria consisting of, for example, the targeting pneumonia bacteria for outpatients and MRSA; *Streptococcus pneumoniae, Haemophilus influenzae, Mycoplasma pneumoniae, Legionella pneumophila*, MRSA, and *Moraxella catarrhalis; Streptococcus pneumoniae, Haemophilus influenzae, Mycoplasma pneumoniae, Chlamydophila pneumoniae*, MRSA, and *Moraxella catarrhalis; Streptococcus pneumoniae, Haemophilus influenzae, Mycoplasma pneumoniae, MRSA, *Staphylococcus aureus*, and *Moraxella catarrhalis*; *Streptococcus pneumoniae*, *Haemophilus influenzae*, *Mycoplasma pneumoniae*, *Legionella pneumophila*, *Chlamydophila pneumoniae*, and *Pseudomonas aeruginosa*; *Streptococcus pneumoniae*, *Haemophilus influenzae*, *Mycoplasma pneumoniae*, *Legionella pneumophila*, *Pseudomonas aeruginosa*, and MRSA; *Streptococcus pneumoniae*, *Haemophilus influenzae*, *Mycoplasma pneumoniae*, *Chlamydophila pneumoniae*, *Pseudomonas aeruginosa*, and MRSA; and *Streptococcus pneumoniae*, *Haemophilus influenzae*, *Mycoplasma pneumoniae*, MRSA, *Staphylococcus aureus*, and *Moraxella catarrhalis*.

Examples of seven types of the targeting pneumonia bacteria can include 120 different combinations of seven types of pneumonia bacteria consisting of, for example, the targeting pneumonia bacteria for outpatients, MRSA, and *Staphylococcus aureus*; the targeting pneumonia bacteria for outpatients, MRSA, and *Moraxella catarrhalis*; *Streptococcus pneumoniae*, *Haemophilus influenzae*, *Mycoplasma pneumoniae*, *Legionella pneumophila*, MRSA, *Staphylococcus aureus*, and *Moraxella catarrhalis*; *Streptococcus pneumoniae*, *Haemophilus influenzae*, *Mycoplasma pneumoniae*, *Chlamydophila pneumoniae*, MRSA, *Staphylococcus aureus*, and *Moraxella catarrhalis*; *Streptococcus pneumoniae*, *Haemophilus influenzae*, *Mycoplasma pneumoniae*, *Pseudomonas aeruginosa*, MRSA, *Staphylococcus aureus*, and *Moraxella catarrhalis*; and *Streptococcus pneumoniae*, *Haemophilus influenzae*, *Pseudomonas aeruginosa*, *Klebsiella pneumoniae*, MRSA, *Staphylococcus aureus*, and *Moraxella catarrhalis*.

Examples of eight types of the targeting pneumonia bacteria can include 90 different combinations of eight types of pneumonia bacteria consisting of, for example, the targeting pneumonia bacteria for outpatients, MRSA, *Staphylococcus aureus*, and *Moraxella catarrhalis*; the targeting pneumonia bacteria for outpatients, *Pseudomonas aeruginosa*, MRSA, and *Staphylococcus aureus*; the targeting pneumonia bacteria for outpatients, *Pseudomonas aeruginosa*, MRSA, and *Moraxella catarrhalis*; *Streptococcus pneumoniae*, *Haemophilus influenzae*, *Mycoplasma pneumoniae*, *Legionella pneumophila*, *Pseudomonas aeruginosa*, MRSA, *Staphylococcus aureus*, and *Moraxella catarrhalis*; and *Streptococcus pneumoniae*, *Haemophilus influenzae*, *Mycoplasma pneumoniae*, *Chlamydophila pneumoniae*, *Pseudomonas aeruginosa*, MRSA, *Staphylococcus aureus*, and *Moraxella catarrhalis*.

Examples of nine types of the targeting pneumonia bacteria can include 10 different combinations of nine types of pneumonia bacteria consisting of, for example, the targeting pneumonia bacteria for outpatients, MRSA, *Staphylococcus aureus*, *Moraxella catarrhalis*, and *Klebsiella pneumoniae*; *Streptococcus pneumoniae*, *Haemophilus influenzae*, *Mycoplasma pneumoniae*, *Legionella pneumophila*, *Pseudomonas aeruginosa*, *Klebsiella pneumoniae*, *Staphylococcus aureus*, MRSA, and *Moraxella catarrhalis*; and *Streptococcus pneumoniae*, *Haemophilus influenzae*, *Mycoplasma pneumoniae*, *Legionella pneumophila*, *Pseudomonas aeruginosa*, MRSA, *Staphylococcus aureus*, and *Moraxella catarrhalis*.

The method for preparing the amplification product in the step (a) is not particularly limited as long as the method involves amplifying single-stranded nucleic acids from target nucleic acids specific for the targeting pneumonia bacteria arbitrarily extracted from a sample possibly containing the targeting pneumonia bacteria, using primers capable of amplifying the corresponding target nucleic acids. Examples of the pneumonia bacterium-specific target nucleic acids can include the nucleic acids of regions contained in *Streptococcus pneumoniae* lytA, *Haemophilus influenzae* dnaJ, *Mycoplasma pneumoniae* dnaJ1, *Chlamydophila pneumoniae* dnaJ, *Staphylococcus aureus* spaA, MRSA mecA, *Legionella pneumophila* dnaJ, *Moraxella catarrhalis* dnaJ, *Pseudomonas aeruginosa* dnaJ, and *Klebsiella pneumoniae* dnaJ.

The primer pairs used in the step (a) or (a') are capable of amplifying the pneumonia bacterium-specific target nucleic acids in the ten types of targeting pneumonia bacteria. These primer pairs comprise target sequences differing among the targeting pneumonia bacteria, wherein the target sequences are selected from the nucleotide sequences represented by SEQ ID NOs: 21 to 40. More specifically, a combination of primer pairs is used, wherein the primer pairs consist of forward and reverse (chimeric) primers and comprise the target nucleotide sequences respectively represented by 5'-CAATCTAGCAGATGAAGCAGG-3' (SEQ ID NO: 21) and 5'-GGTTGTTTGGTTGGTTATTCG-3' (SEQ ID NO: 31) for *Streptococcus pneumoniae*, 5'-TCAATACTCTTG-CACATTGTGAT-3' (SEQ ID NO: 22) and 5'-ATACGAA-GAAACCTTGCTGAC-3' (SEQ ID NO: 32) for *Haemophilus influenzae*, 5'-CCGGGATGGTTAGCTGTAACAG-3' (SEQ ID NO: 23) and 5'-TACCTTCTTGTACTTACTTCC-3' (SEQ ID NO: 33) for *Mycoplasma pneumoniae*, 5'-CATG-GTGTTGAGAAGGAACTTGTAGT-3' (SEQ ID NO: 24) and 5'-TCCACGACTCTGTACCACTTG-3' (SEQ ID NO: 34) for *Chlamydophila pneumoniae*, 5'-CGTCAAT-CACGTGGACAAAGAG-3' (SEQ ID NO: 25) and 5'-AG-TACCATGTCTTGGAACGGT-3' (SEQ ID NO: 35) for *Legionella pneumophila*, 5'-GAAGTTCCGATCAACT-TCAC-3' (SEQ ID NO: 26) and 5'-AAGCTCTCCT-GAAGCTCTTT-3' (SEQ ID NO: 36) for *Klebsiella pneumoniae*, 5'-ACAGGGATCGGAAATCAT-3' (SEQ ID NO: 27) and 5'-CGCGGACCTGCGCTACACCCTGGACC-3' (SEQ ID NO: 37) for *Pseudomonas aeruginosa*, 5'-CAAAGGCT-TGCCCAAAGATA-3' (SEQ ID NO: 28) and 5'-GAAGC-CGAAGAAAAGCTCAA-3' (SEQ ID NO: 38) for *Moraxella catarrhalis*, 5'-GTATGTGGAAGTTAGAT-TGGG-3' (SEQ ID NO: 29) and 5'-GATACATTCTTTG-GAACGAT-3' (SEQ ID NO: 39) for MRSA, and 5'-GAGTA-CATGTCGTTAAACCTGGTG-3' (SEQ ID NO: 30) and 5'-TACAGTTGTACCGATGAATGG-3' (SEQ ID NO: 40) for *Staphylococcus aureus*. Alternatively, a combination of primer pairs may be used, wherein the primer pairs consist of forward and reverse (chimeric) primers and comprise the target nucleotide sequences respectively represented by 5'-AGCGTATGAAATCCTGACTGAT-3' (SEQ ID NO: 54) and 5'-CAAAGATATCGCTGAAGTCG-3' (SEQ ID NO: 56) for *Klebsiella pneumoniae*, and 5'-GCGAGGTGTCGCTCT-GCAAC-3' (SEQ ID NO: 55) and 5'-GATGTGCAAGGTG-GTGGTGGA-3' (SEQ ID NO: 57) for *Pseudomonas aeruginosa* instead of the sequences described above.

Primers consisting of the nucleotide sequence represented by any of SEQ ID NOs: 21 to 30, 54, and 55 are used as the forward primers. A tag sequence can be added to the respective 5' ends of these ten types of target sequences differing by the targeting pneumonia bacteria. Examples of the tag sequence can include 5'-TAGCAGGATCCCTCTAAG-3' (SEQ ID NO: 41). Primers consisting of the nucleotide sequence represented by any of SEQ ID NOs: 31 to 40, 56, and 57 and an RNA polymerase promoter sequence added to the respective 5' ends of these ten types of target sequences differing among the targeting pneumonia bacteria are used as the reverse primers. Examples of the RNA polymerase promoter sequence can include T7 RNA polymerase promoter sequences, T3 RNA polymerase promoter sequences, and SP6 RNA polymerase promoter sequences. Among them, T7 RNA polymerase promoter sequences are preferable in terms of high RNA amplification efficiency. Examples of the T7 RNA polymerase promoter sequences can include 5'-AAT-TCTAATACGACTCACTATAGGGAG-3' (SEQ ID NO: 42) and 5'-CTAATACGACTCACTATAGGGAG-3' (SEQ ID NO: 43). A nucleotide sequence derived from the nucleotide sequence represented by any of SEQ ID NOs: 21 to 40 and 54 to 57 by the deletion, substitution, or addition of one or more (e.g. 1 to 5, preferably 1 to 3, more preferably 1 or 2, further preferably 1) bases may be used as a primer in the present invention as long as this primer is capable of amplifying the corresponding pneumonia bacterium-specific target nucleic acid. The forward and reverse primers can be synthesized by a routine method using a DNA synthesizer or the like.

Examples of the test sample possibly containing the nucleic acids of the targeting pneumonia bacteria in the step (a) or (b') can include pneumonia patient's saliva, sputum, peripheral blood, bronchoalveolar lavage, nasal lavage fluid, gargled fluid, and nasopharyngeal swab, and microbes contained therein, and cell lysates of cultures of the microbes. A method known in the art, such as an RNA extraction method using guanidine thiocyanate and a nucleic acid extraction method using EDTA-SDS-phenol-ethanol can be used as the method for extracting the nucleic acids from the test sample. Alternatively, a commercially available product such as Extragen II (manufactured by Tosoh Corp.) or Mora-Extract (manufactured by AMR Inc.) can be used. The extracted RNAs or DNAs can be cleaved appropriately to prepare one or more RNAs or DNAs comprising the 5'-sequence and target-specific 3'-sequence of each target RNA or target DNA.

When the target nucleic acids are target RNAs, the target nucleic acids used in the step (a) or (b') can be amplified using an RNA amplification method known in the art, such as an NASBA method, transcription-mediated amplification (TMA), or transcription-reverse transcription concerted reaction (TRC) method. An NASBA method, particularly, the NASBA method described in International Publication No. WO 2009/057330, can be used advantageously in the present invention. This NASBA method involves amplifying a target RNA in a sample via RNA polymerase or reverse transcriptase. For example, the NASBA method disclosed in International Publication No. WO 2009/057330 consists of the steps of: (A) immobilizing the 5' end of a chimeric primer represented by any of SEQ ID NOs: 1 to 10 onto the surface of a substrate to prepare a solid-phase DNA (+) primer, wherein the chimeric primer comprises a DNA sequence corresponding to a target-specific 5'-sequence of the target RNA; (B) adding a T7 RNA polymerase promoter sequence to the 5' end of a primer comprising a cDNA sequence complementary to a 3'-sequence of the target RNA to prepare a liquid-phase cDNA (−) primer represented by any of SEQ ID NOs: 11 to 20; (B') optionally adding an RNA polymerase promoter sequence to the 5' end of a tag sequence to prepare a liquid-phase universal primer; (C) preparing a sample RNA comprising the 3'-sequence and the target-specific 5'-sequence of the target RNA; (D) contacting the liquid-phase cDNA (−) primer prepared in step (B) with the sample RNA strand prepared in step (C) in a liquid phase to hybridize the liquid-phase cDNA (−) primer with the sample RNA, and then extending a DNA (−) strand using reverse transcriptase to prepare a cDNA strand-RNA strand complex; (E) allowing an RNase to act on the cDNA strand-RNA strand complex prepared in step (D) to prepare a single-stranded DNA (−), wherein the RNase specifically degrades the RNA strand in the DNA strand-RNA strand complex; (F) contacting the single-stranded DNA (−) prepared in step (E) with the solid-phase DNA (+) primer prepared in step (A) in a liquid phase to hybridize the single-stranded DNA (−) with the solid-phase DNA (+) primer, and then extending a DNA (+) strand using an enzyme having a DNA-dependent activation potency of DNA polymerase, to prepare a double-stranded DNA; and (G) allowing RNA polymerase to act on the double-stranded DNA prepared in step (F) to amplify a single-stranded RNA (−) by use of the RNA polymerase promoter sequence derived from the DNA (−) strand.

When the target nucleic acids are target DNAs, the target nucleic acids used in the step (a) or (b') can also be amplified using, for example, an NASBA, PCR, strand displacement amplification (SDA), or ligase chain reaction (LCR) method. In this case, primers selected from the nucleotide sequences represented by SEQ ID NOs: 21 to 30, 54, and 55 are used as the forward primers, and primers comprising the nucleotide sequence represented by any of SEQ ID NOs: 31 to 40, 56, and 57 are used as the reverse primers.

The probe pairs used in the step (b) are probe pairs differing among the pneumonia bacteria, wherein the probe pairs are selected from nucleotide sequences complementary to amplification products, for example, the nucleotide sequences represented by SEQ ID NOs: 1 to 20. For the sake of convenience, these sequences are indicated as DNA sequences in the Sequence Listing. In this context, the probe pairs of the present invention may consist of the nucleotide sequences of DNAs or may consist of nucleotide sequences of RNAs. However, probe pairs consisting of the nucleotide sequences of DNAs are preferable because of excellent stability as probes.

The probe pairs differing by the targeting pneumonia bacteria can be specifically exemplified by combinations of: 5'-ACGCACGAGTATTGCACGAATAACC-3' (SEQ ID NO: 1) and 5'-TGCCGAAAACGCTTGATACAGGGAGT-3' (SEQ ID NO: 11) for *Streptococcus pneumoniae*; 5'-AAACT-TGTCCGCATTGCCACGGTTC-3' (SEQ ID NO: 2) and 5'-CTCTGGGGCTGAAAAAGGTTCTAAAG-3' (SEQ ID NO: 12) for *Haemophilus influenzae*; 5'-AGGCCAAACA-CAAGTGTAAGACTTG-3' (SEQ ID NO: 3) and 5'-AGAAT-CAACGCTCCATCTTTGGTAC-3' (SEQ ID NO: 13) for *Mycoplasma pneumoniae*; 5'-ATCTTGTGAAACCTGT-TCTGGTCAA-3' (SEQ ID NO: 4) and 5'-TCAAGGGAT-TAAATCCTGCGAACGT-3' (SEQ ID NO: 14) for *Chlamydophila pneumoniae*; 5'-GAAGTTGAAATTACCGTTCCAAGAC-3' (SEQ ID NO: 5) and 5'-CAATTGACCCTTGAAGAAGCAGCTA-3' (SEQ ID NO: 15) for *Legionella pneumophila*; 5'-GTGGTG-GAGACGCCGGTGGGGCTGA-3' (SEQ ID NO: 6) and 5'-TGAAACCCAGACCGGCAAGCTGTTC-3' (SEQ ID NO: 16) for *Klebsiella pneumoniae*; 5'-GGTGACCGGT-GTGGTGCCGG-3' (SEQ ID NO: 7) and 5'-GTCTTG-CAACCGACCAGGGTCGGCA-3' (SEQ ID NO: 17) for *Pseudomonas aeruginosa*; 5'-GGTTGCGCGTTTTTCAG-GATCACTG-3' (SEQ ID NO: 8) and 5'-CCACCAGAGC-CCATGCCTTGTTCAT-3' (SEQ ID NO: 18) for *Moraxella catarrhalis*; 5'-AGACCGAAACAATGTGGAATTGGC-3' (SEQ ID NO: 9) and 5'-ATGCAGAAAGACCAAAGCATA-CATAT-3' (SEQ ID NO: 19) for MRSA; and 5'-CATGAT-CAAACCTGGTCAAGAACTTG-3' (SEQ ID NO: 10) and 5'-CGGCACTACTGCTGACAAAATTGCT-3' (SEQ ID NO: 20) for *Staphylococcus aureus*. Alternatively, combinations of 5'-AACTTGTCCGCATTGCCACGGTTCT-3' (SEQ ID NO: 44) and 5'-TGTGATAGCTGTGGTG-GCTCTGGGG-3' (SEQ ID NO: 49) for *Haemophilus influenzae*, 5'-TCAAGGGATTAAATCCTGCGAACGT-3' (SEQ ID NO: 45) and 5'-ATCTTGTGAAACCTGTTCTGGT-CAA-3' (SEQ ID NO: 50) for *Chlamydophila pneumoniae*, 5'-AAGAAGCAGCTATAGGAAAAGAAGT-3' (SEQ ID NO: 46) and 5'-GGGGCGCTGATTTGCAATTTAATGT-3'

(SEQ ID NO: 51) for *Legionella pneumophila*, 5'-TCGAA-CAGGGCGGCATGGGCGGCGG-3' (SEQ ID NO: 47) and 5'-CAGAAGCGTGCGGCCTACGATCAGT-3' (SEQ ID NO: 52) for *Klebsiella pneumoniae*, and 5'-TCCAGGT-TCACCGGGGTTTCCACC-3' (SEQ ID NO: 48) and 5'-GCTCTGCAACGACTTGCGGAACTC-3' (SEQ ID NO: 53) for *Pseudomonas aeruginosa* may be used as the probe pairs.

Which strands to select as the first probe in the step (c) or the second probe in the step (d) in these ten types of probe pairs can be determined appropriately according to, for example, the targeting pneumonia bacteria presumed to be present in the sample. A nucleotide sequence derived from the nucleotide sequence represented by any of SEQ ID NOs: 1 to 20 and 44 to 53 by the deletion, substitution, or addition of one or more (e.g., 1 to 5, preferably 1 to 3, more preferably 1 or 2, further preferably 1) bases may be used as a probe in the present invention as long as the probe is capable of detecting the corresponding pneumonia bacterium-specific target nucleic acid.

Figure 13:
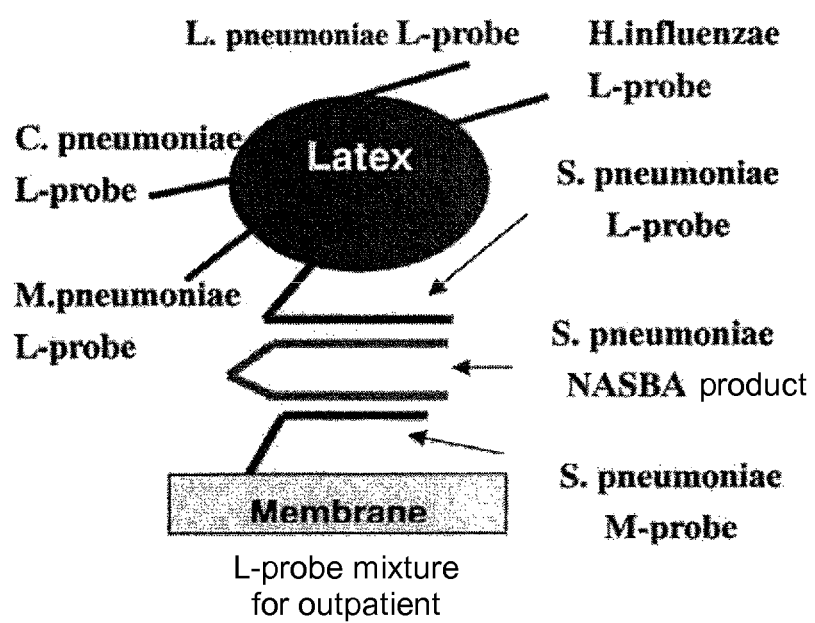
FIG. 13 is a schematic diagram showing one specific example of a nucleic acid chromatography of the present invention.

Examples of the first probe in the step (c) can include at least three types of probes to be paired with the second probe, for example, first probes for at least three types, preferably at least five types of pneumonia bacteria, to be paired with the second probes, wherein the first probes are selected from the nucleotide sequences represented by SEQ ID NOs: 1 to 10. For example, two sets of first probe-bound labeled high molecular carriers in which first probes for five types of pneumonia bacteria are bound to each labeled high molecular carrier may be used at the same time. Examples of the method for binding the plural types of first probes to the labeled high molecular carrier can include a method involving binding DNAs having the nucleotide sequence represented by any of SEQ ID NOs: 1 to 10 and an additional group introduced at the 5' or 3' end thereof to a labeled high molecular carrier having an additional group introduced therein. Examples of the additional group can include amino, carboxyl, hydroxyl, and thiol groups. For example, amino groups are preferable for a labeled high molecular carrier modified with carboxyl groups. Since plural types of first probes are bound to one labeled high molecular carrier, this approach does not require, for the detection, the conventional procedure of mixing a plurality of first probe-bound labeled high molecular carriers in which one type of first probe is bound to each labeled high molecular carrier. Thus, this approach is preferable not only in terms of convenient detection operation but because the concentration of the labeled high molecular carrier described below such as a labeled latex can be set to the optimum concentration. One specific example of the present invention is shown in FIG. 13 in the form of a schematic diagram.

Examples of the high molecular carrier in the labeled high molecular carrier can include: hydrophilic resins such as carboxymethylcellulose (CMC) and polyacrylate having a carboxyl group; and latices such as acrylic latex, polyester latex, polystyrene latex, polyurethane latex, polyvinyl acetate latex, SBR resin, NBR resin, polyamide latex, and carboxy-modified polystyrene latex. When an amino group is introduced in the nucleotide sequences represented by SEQ ID NOs: 1 to 10, carboxy-modified polystyrene latex in which a carboxyl group is introduced in polystyrene latex is preferable because the first probes for at least three types, preferably at least five types of pneumonia bacteria, selected from the nucleotide sequences represented by SEQ ID NOs: 1 to 10 can be bound easily to the labeled high molecular carrier through reaction forming covalent bond via the amino group and the carboxyl group. Specifically, carboxyl group-containing polystyrene latex (solid content: 4% (w/w)) (manufactured by Duke Scientific Corp.) or carboxyl group-containing polystyrene latex (solid content: 10% (w/w)) (manufactured by Bangs Laboratories, Inc.) can be used.

Specific examples of the method for preparing the first probe-bound labeled high molecular carrier in which the plural types of first probes are bound to the labeled high molecular carrier can include a method involving: mixing first probes for the at least three types of pneumonia bacteria, carboxyl group-containing polystyrene latex (manufactured by Bangs Laboratories, Inc.), and water-soluble carbodiimide in a 50 mM MES (2-morpholinoethanesulfonic acid, monohydrate) (manufactured by Dojindo Laboratories) buffer solution to bind carboxyl groups in the latex to amino groups in the first probes, wherein the first probes are selected from the nucleotide sequences represented by SEQ ID NOs: 1 to 10 and have an amino group introduced at the 5' end thereof; then further reacting the mixture by the addition of monoethanolamine (manufactured by Wako Pure Chemical Industries, Ltd.); centrifuging the reaction solution, followed by removal of the supernatant; and washing and resuspending the obtained precipitate with a HEPES (2-[4-(2-hydroxyethyl)-1-piperazinyl] ethanesulfonic acid) (manufactured by Saikyo Kasei Co., Ltd.) buffer solution containing a nonionic surfactant to prepare a first-probe-bound labeled high molecular carrier. Also, the particle size of the high molecular carrier can be selected appropriately and is preferably selected from particle sizes smaller than the pore size of a membrane. For example, particles having a size of 500 nm or smaller (in terms of diameter) can be selected.

A high molecular carrier that exhibits a color distinguishable from that of the developing support may be used as the labeled high molecular carrier. A high molecular carrier colored with a pigment or the like can also be used. Alternatively, a fluorescently labeled high molecular carrier may be used.

Examples of the second probe in the step (d) can include at least three types of probes to be paired with the first probe, for example, second probes for at least three types, preferably at least five types of pneumonia bacteria, to be paired with the first probes, wherein the second probes are selected from the nucleotide sequences represented by SEQ ID NOs: 11 to 20. These second probes are immobilized on a support. One type of second probe may be immobilized at the predetermined positions on one support (for exclusive use), or plural types of second probes may be immobilized at the predetermined positions on one support (for shared use). Examples of the method for preparing the second probe-carrying developing support can include a method involving immobilizing second probes to their respective predetermined positions distinguishable among the pneumonia bacteria on a developing support, for example, a method involving immobilizing probes having the nucleotide sequence represented by any of SEQ ID NOs: 11 to 20 and an additional group introduced at the 5' or 3' end thereof to a developing support. Examples of the additional group can include amino, carboxyl, hydroxyl, and thiol groups. For example, amino groups are preferable for a developing support modified with carboxyl groups. The second probe can be prepared using a method known in the art, such as a chemical synthesis method, irrespective of the presence or absence of the introduced additional group.

Examples of the developing support can include nylon membranes, nylon membrane derivatives such as carboxyl group-modified nylon membranes, cellulose membranes, and cellulose membrane derivatives such as nitrocellulose membranes. When an amino group is introduced in the nucleotide sequences represented by SEQ ID NOs: 11 to 20, a carboxyl group-modified nylon membrane is preferable because the second probes for at least three types, preferably at least five types of pneumonia bacteria, selected from the nucleotide sequences represented by SEQ ID NOs: 11 to 20 can be bound easily to their respective predetermined positions distinguishable among the pneumonia bacteria on the developing support through reaction forming covalent bond via the amino group and the carboxyl group.

Specific examples of the method for preparing the second probe-carrying developing support can include a method involving: activating a carboxyl group-modified nylon membrane by treatment with water-soluble carbodiimide and washing with deionized water; immobilizing nucleotides having the second probe sequence to their respective predetermined positions appropriately assigned to be distinguishable among the pneumonia bacteria on the carboxyl group-modified nylon membrane thus activated; drying the resulting membrane in air for minutes; then treating, with a Tris-based buffer solution, the carboxyl group-modified nylon membrane carrying the immobilized nucleotides having the second probe sequence, to eliminate active groups; washing the nucleotide-immobilized membrane with deionized water to prepare a second probe-carrying developing support. The manner in which the nucleotides having the second probe sequence are immobilized is not particularly limited and may be a linear or round spot pattern.

The method for detecting the amplification products in the step (e) is not particularly limited as long as the method involves hybridizing the amplified single-stranded nucleic acids with the second probe carried by the developing support and the first probe bound to the labeled high molecular carrier, followed by the detection. It is preferred to allow a retainer in advance to retain the first probe-bound labeled high molecular carrier in which the plural types of first probe are bound to the labeled high molecular carrier. Preferable examples of the retainer can include absorbent pads manufactured by Advantec Toyo Kaisha, Ltd. The retainer (consisting of, e.g., an absorbent pad) retaining the first probe-bound labeled high molecular carrier can be connected sequentially to the other end of the second probe-carrying developing support to prepare a test strip for nucleic acid chromatography, which can be used advantageously in the detection method of the present invention. Examples of the method for preparing the retainer can include a method involving applying, to the retainer, the labeled high molecular carrier bound to plural types of nucleotides having the first probe sequence, followed by drying.

The method for hybridizing the amplification products obtained in the step (a) to the second probe carried by the developing support and the first probe bound to the labeled high molecular carrier, followed by detection in the step (e) involves, for example, dipping the test strip for nucleic acid chromatography in a solution containing the amplification products. When the first probe-bound labeled high molecular carrier soaks into the developing support from the retainer and reaches the predetermined positions at which the second probe for the targeting pneumonia bacteria to be paired with the first probe are immobilized on the developing support, the amplification products can be captured at the predetermined positions by sandwich hybridization. Even in the presence of plural types of target single-stranded nucleic acids in the amplification products, these target nucleic acids can be captured sequentially by their second probe at the predetermined positions.

Subsequently, in the step (f), the labeled high molecular carrier bound to the nucleotides having the first probe sequence reaches the predetermined positions at which the nucleotides having the second probe sequence are immobilized on the developing support and accumulates at the positions. The presence or absence of colored lines, colored spots, or the like appearing at the predetermined positions can be judged and thereby evaluated either directly from the detection image or with a fluorescence visualization apparatus. The targeting pneumonia bacteria (pneumonia causative bacteria) can be detected on the basis of the evaluation. This judgment is preferably visual judgment in terms of convenience.

Alternatively, nucleotides consisting of the sequences represented by SEQ ID NOs: 44 to 48 may be used instead of or in addition to the first probes consisting of the sequences represented by SEQ ID NOs: 1 to 10. Likewise, nucleotides consisting of the sequences represented by SEQ ID NOs: 49 to 53 may be used instead of or in addition to the second probes consisting of the sequences represented by SEQ ID NOs: 11 to 20.

Examples of the method for qualitatively or quantitatively detecting the target nucleic acids in the step (c') can include electrophoresis, hybridization, and sequencing. Examples of the electrophoresis method can include a method involving analyzing the molecular weights of the amplification products by molecular sieve effect using an agarose gel, and Agilent Technologies analysis system using capillary electrophoresis. Examples of the hybridization method can include a method involving monitoring and analyzing in real time the formation process of the amplification products using a reagent for real-time monitoring, as in real-time PCR. Examples of the reagent for real-time monitoring can include TaqMan (registered trademark; manufactured by Applied Biosystems, Inc.) probes. The hybridization method may encompass Northern blotting. Examples of the sequencing method can include the dideoxy method, which stops DNA polymerase-mediated synthesis in a base-specific manner using dideoxynucleotide.

The kit for detecting pneumonia causative bacteria of the present invention can be used in the method for detecting pneumonia causative bacteria of the present invention. Examples thereof can include a kit comprising at least three types, preferably at least five types, i.e., five to ten types of primer pairs differing among the pneumonia bacteria, which are capable of amplifying pneumonia bacterium-specific target nucleic acids arbitrarily extracted from a sample, wherein the primer pairs are selected from a forward primer consisting of the nucleotide sequence represented by SEQ ID NO: 21 and a reverse primer consisting of the nucleotide sequence represented by SEQ ID NO: 31 and an RNA polymerase promoter sequence added to the 5' end thereof; a forward primer consisting of the nucleotide sequence represented by SEQ ID NO: 22 and a reverse primer consisting of the nucleotide sequence represented by SEQ ID NO: 32 and an RNA polymerase promoter sequence added to the 5' end thereof; a forward primer consisting of the nucleotide sequence represented by SEQ ID NO: 23 and a reverse primer consisting of the nucleotide sequence represented by SEQ ID NO: 33 and an RNA polymerase promoter sequence added to the 5' end thereof; a forward primer consisting of the nucleotide sequence represented by SEQ ID NO: 24 and a reverse primer consisting of the nucleotide sequence represented by SEQ ID NO: 34 and an RNA polymerase promoter sequence added to the 5' end thereof; a forward primer consisting of the nucleotide sequence represented by SEQ ID NO: 25 and a reverse primer consisting of the nucleotide sequence represented by SEQ ID NO: 35 and an RNA polymerase promoter sequence added to the 5' end thereof; a forward primer consisting of the nucleotide sequence represented by SEQ ID NO: 26 and a reverse primer consisting of the nucleotide sequence represented by SEQ ID NO: 36 and an RNA polymerase promoter sequence added to the 5' end thereof; a forward primer consisting of the nucleotide sequence represented by SEQ ID NO: 27 and a reverse primer consisting of the nucleotide sequence represented by SEQ ID NO: 37 and an RNA polymerase promoter sequence added to the 5' end thereof; a forward primer consisting of the nucleotide sequence represented by SEQ ID NO: 28 and a reverse primer consisting of the nucleotide sequence represented by SEQ ID NO: 38 and an RNA polymerase promoter sequence added to the 5' end thereof; a forward primer consisting of the nucleotide sequence represented by SEQ ID NO: 29 and a reverse primer consisting of the nucleotide sequence represented by SEQ ID NO: 39 and an RNA polymerase promoter sequence added to the 5' end thereof; a forward primer consisting of the nucleotide sequence represented by SEQ ID NO: 30 and a reverse primer consisting of the nucleotide sequence represented by SEQ ID NO: 40 and an RNA polymerase promoter sequence added to the 5' end thereof; a forward primer consisting of the nucleotide sequence represented by SEQ ID NO: 54 and a reverse primer consisting of the nucleotide sequence represented by SEQ ID NO: 56 and an RNA polymerase promoter sequence added to the 5' end thereof; and a forward primer consisting of the nucleotide sequence represented by SEQ ID NO: 55 and a reverse primer consisting of the nucleotide sequence represented by SEQ ID NO: 57 and an RNA polymerase promoter sequence added to the 5' end thereof. This kit may comprise, in addition to the primer pairs, various reagents for use in the RNA amplification method in the step (b') or various reagents for use for qualitatively or quantitatively detecting the target nucleic acid in the step (c'). Alternatively, the kit of the present invention may comprise: an amplification set for amplifying single-stranded nucleic acids using primers from pneumonia bacterium-specific target nucleic acids arbitrarily extracted from a sample; a first probe-bound labeled high molecular carrier in which first probes for the at least three types of pneumonia bacteria are bound to a labeled high molecular carrier, wherein the first probes are selected from nucleotide sequences complementary to amplification products, for example, the nucleotide sequences represented by SEQ ID NOs: 1 to 10 and 44 to 48; and a second probe-carrying developing support for exclusive use in each type of pneumonia bacteria or for shared use in plural types of pneumonia bacteria in which second probes to be paired with the first probes, for example, second probes for the at least three types of pneumonia bacteria selected from the nucleotide sequences represented by SEQ ID NOs: 11 to 20 and 49 to 53, are immobilized at their respective predetermined positions distinguishable among the pneumonia bacteria. Preferable examples thereof can include a kit comprising the amplification set and the test strip for nucleic acid chromatography. This kit can be used preferably in the method for detecting pneumonia causative bacteria of the present invention.

Hereinafter, this invention will be described more specifically with reference to Examples. However, the scope of this invention is not intended to be limited to these examples.

EXAMPLES

Design of *Moraxella catarrhalis* dnaJ Primers

The genome information of *Moraxella catarrhalis* had not yet been completely decoded. Although primer design was pursued on the basis of the dnaJ gene sequence of a strain of related genus, primers specific for this bacterium were difficult to design. Meanwhile, only the genomic sequence information of this bacterium has been revealed in recent years. Thus, the annotation of the dnaJ gene based on this genomic sequence was carried out by ORF extraction using alignment software DNASISpro (manufactured by Hitachi Software Engineering Co., Ltd.). The design of novel primers was attempted from this sequence. The novel primers were verified using eight *Moraxella catarrhalis* strains. A reagent kit TaKaRa PCR Thermal Cycler GP was used according to the protocol described therein. PCR was carried out under conditions involving 95° C. for 3 min and (95° C. for 10 sec, 65° C. for 10 sec, and 72° C. for 10 sec)×40 cycles using EX Taq Hot start (manufactured by Takara Bio Inc.) as an instrument. The obtained PCR products were analyzed by electrophoresis using MultiNA. The electrophoresis results are shown in FIG. 1. The obtained PCR products were successfully amplified for all the bacterial strains, demonstrating that the newly designed primer pair is useful in the detection of *Moraxella catarrhalis*.

[Study on Multiplexing]
(Preparation of Template RNA)

Since *Mycoplasma pneumoniae* and *Chlamydophila pneumoniae* are difficult to culture, template RNAs were prepared by DNA cloning using plasmid vectors. Target gene regions were cloned to prepare recombinants. First, each DNA fragment of the target gene dnaJ in *Mycoplasma pneumoniae* or *Chlamydophila pneumoniae* was inserted to plasmid vectors. Host *E. coli* was transformed with each resulting plasmid vector. After plasmid extraction from *E. coli*, the target genes were DNA-amplified by PCR. From the obtained PCR products, RNAs were amplified using RiboMAX (registered trademark) T7 Express system (manufactured by Promega Corp.) according to the protocol. The obtained RNAs were used as templates in the NASBA method. RNAs from targeting pneumonia causative bacteria other than *Mycoplasma pneumoniae* and *Chlamydophila pneumoniae* were prepared by a routine method.

(RNA Amplification of Target Gene by NASBA Method)

TAGCAGGATCCCTCTAAG (SEQ ID NO: 41) was added to the respective 5' ends of target sequences selected according to targeting pneumonia bacteria from the nucleotide sequences represented by SEQ ID NOs: 21 to 40 to prepare ten types of primers for use as forward primers. CTAATACGACTCACTATAGGGAG (SEQ ID NO: 43) was added as a T7 RNA polymerase promoter sequence to the respective 5' ends of target sequences differing among the pneumonia bacteria to prepare ten types of promoters for use as reverse primers. The NASBA method was carried out for each individual bacterial strain with RNAs extracted from 7 types of the standard strains (*Streptococcus pneumoniae, Legionella pneumophila, Klebsiella pneumoniae, Moraxella catarrhalis, Staphylococcus aureus, Mycoplasma pneumoniae*, and *Chlamydophila pneumoniae*) as templates to separately amplify the RNAs of the target genes. The obtained data is shown. The RNA extraction was carried out using MORA-EXTRACT (manufactured by AMR Inc.) according to the protocol included therein. The NASBA method was carried out using NASBA Amplification kit (manufactured by KAINOS Laboratories, Inc.) according to the protocol included therein. The RNA samples used as the respective templates for *Streptococcus pneumoniae, Mycoplasma pneumoniae, Chlamydophila pneumoniae, Legionella pneumophila, Klebsiella pneumoniae, Moraxella catarrhalis*, and *Staphylococcus aureus* were separately diluted at a ratio of 1, 1/10, 1/100, or 1/1000 and analyzed using Bio Analyzer;

Agilent RNA Pico 6000. An enzyme-free reaction solution was prepared as a control to carry out similar steps. The results are shown in FIGS. 2 to 8. RNA amplification by the NASBA method was confirmed for all the target strains of the targeting pneumonia causative bacteria.

(Verification of Specificity of Each Primer)

The presence or absence of nonspecific reaction of each primer with a bacterium other than its target was verified after multiplexing of the ten primer pairs of this case. The results are shown in FIG. 9. Nonspecific reaction was not observed for all the primers in the ten primer pairs of this case.

(Amplification of Target RNA by NASBA Method Using Multiplex Primers)

Figure 10:
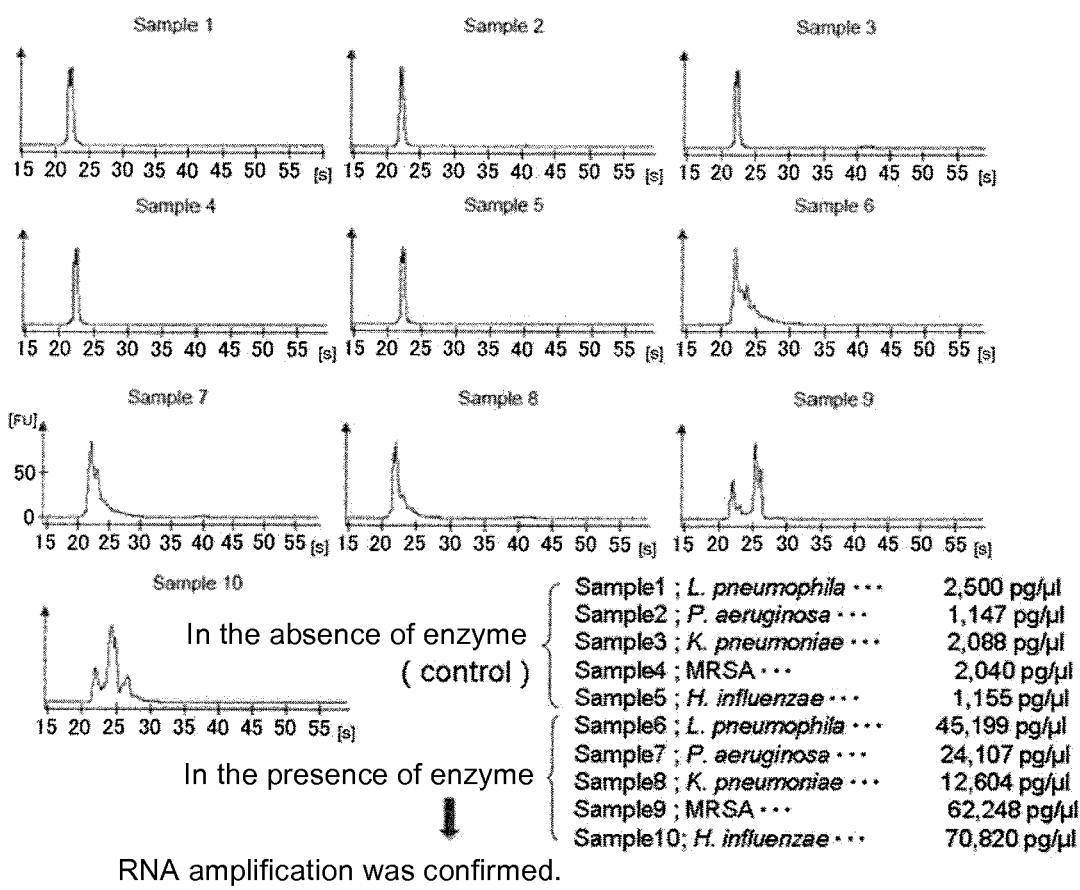
FIG. 10 is a diagram showing that target RNA amplification products by the NASBA method using multiplex primers were detected for *Legionella pneumophila, Pseudomonas aeruginosa, Klebsiella pneumoniae*, MRSA, and *Haemophilus influenzae*.
Figure 11:
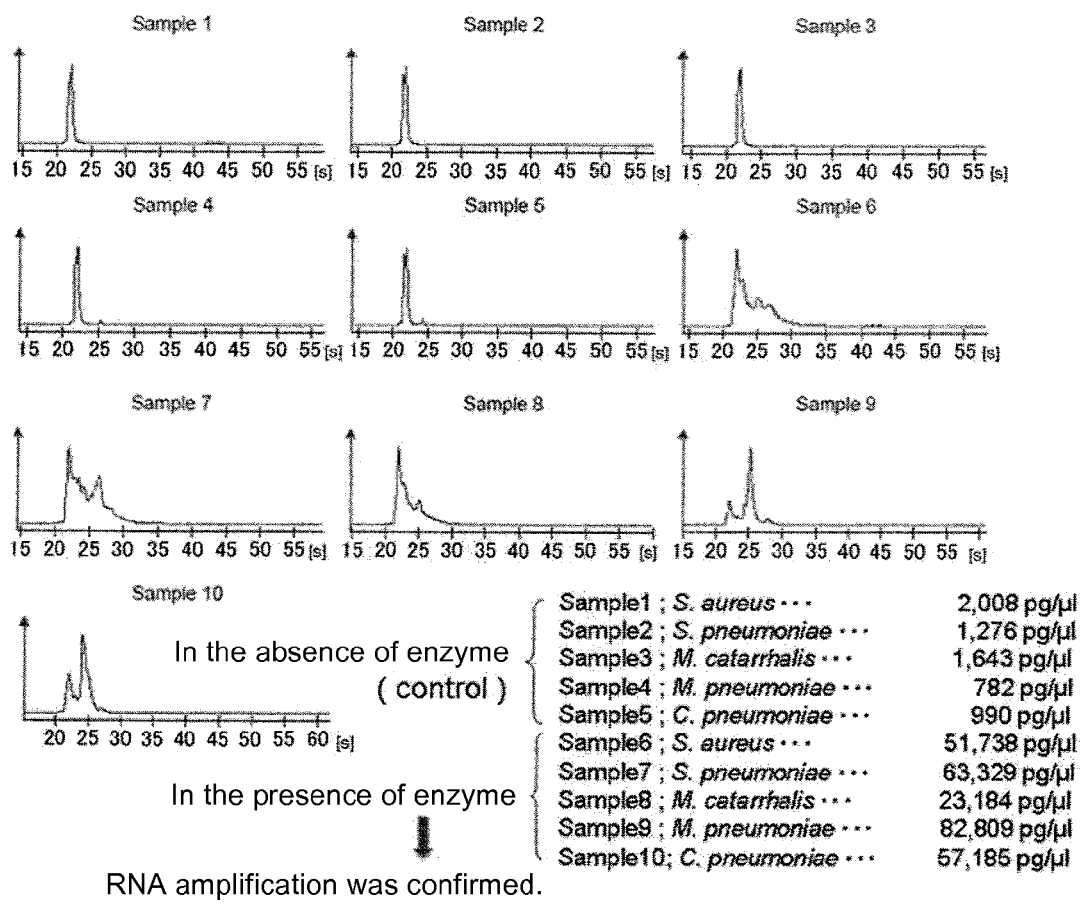
FIG. 11 is a diagram showing that target RNA amplification products were detected for *Staphylococcus aureus, Streptococcus pneumoniae, Moraxella catarrhalis, Mycoplasma pneumoniae*, and *Chlamydophila pneumoniae* after the RNA amplification by the NASBA method using multiplex primers including a primer pair directed to each bacterium.

Results of studying the multiplexing of the primer pairs of this case for *Legionella pneumophila*, *Pseudomonas aeruginosa*, *Chlamydophila pneumoniae*, MRSA, and *Haemophilus influenzae* are shown in FIG. 10. Likewise, results of studying the multiplexing of the primer pairs of this case for *Staphylococcus aureus*, *Streptococcus pneumoniae*, *Moraxella catarrhalis*, *Mycoplasma pneumoniae*, and *Chlamydophila pneumoniae* are shown in FIG. 11. It was confirmed that the RNAs of the target strains of the targeting pneumonia causative bacteria were all amplified by the NASBA method.

(Confirmation of NASBA Product)

Figure 12:
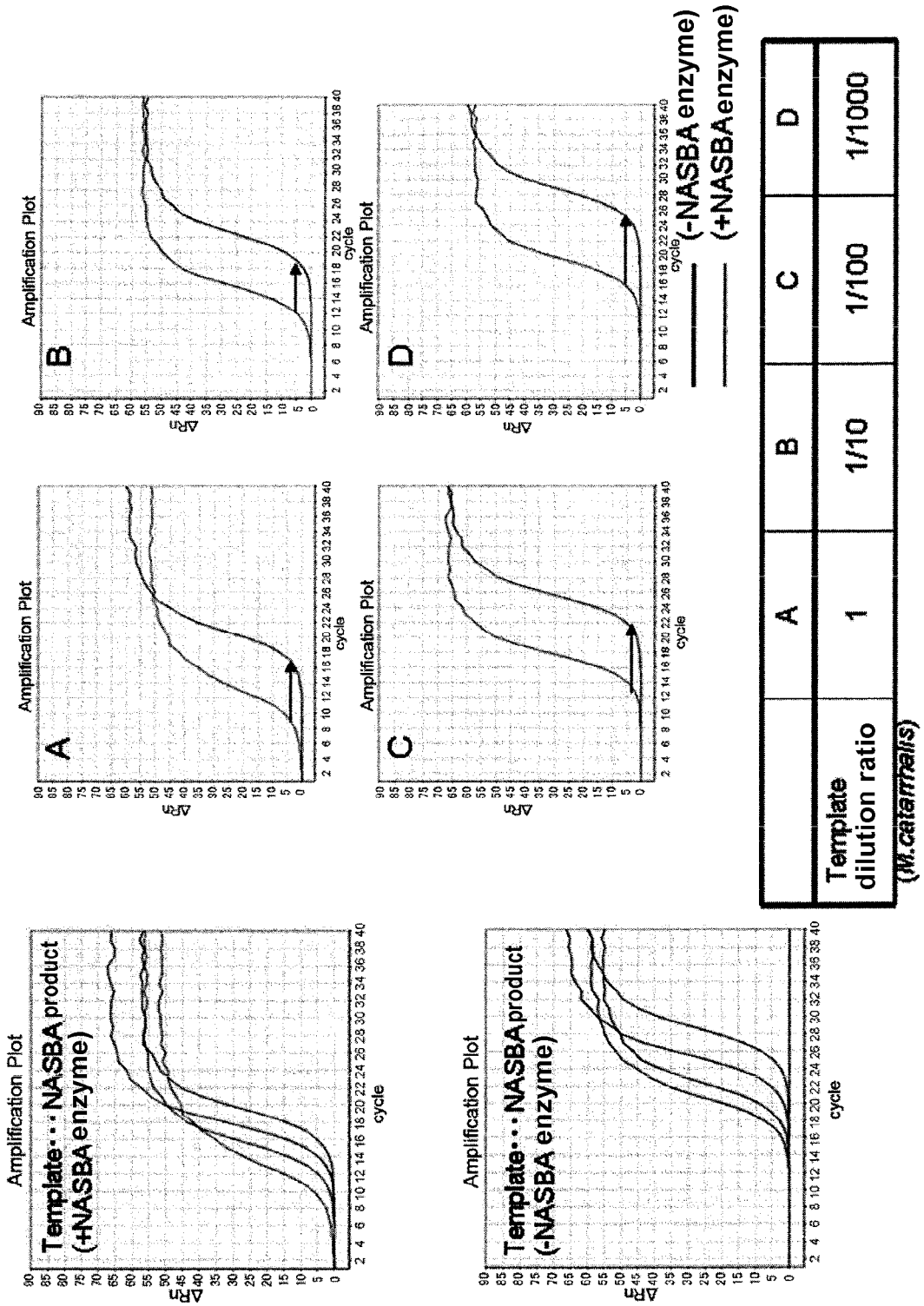
FIG. 12 is a diagram showing that *Moraxella catarrhalis*-derived RNA amplified by NASBA was confirmed by real-time PCR to be the target NASBA product of interest.

It is necessary to determine whether RNAs amplified by NASBA have the target sequence of interest. Real-time PCR was carried out targeting DNAs synthesized as by-products of the NASBA reaction. The Ct values of the NASBA products and control samples unreacted by NASBA were measured, and the difference therebetween was compared to indirectly confirm the target NASBA products. PCR was performed under conditions involving 95° C. for 3 min and (95° C. for 10 sec, 65° C. for 10 sec, and 72° C. for 10 sec)×40 cycles using SYBR premix EX Taq Hot start (manufactured by Takara Bio Inc.) according to the protocol. For all the bacterial strains, the RNAs amplified by NASBA were indirectly confirmed to be the target NASBA products of interest. The results about *Moraxella catarrhalis* are shown in FIG. 12.

[Determination of Probe Pair]

An attempt was made to prepare one pair of amino group-containing oligonucleotide probes having a sequence complementary to the target nucleic acid sequence in the gene region shown in Table 1 below in each targeting pneumonia bacterium.

TABLE 1

| Name of bacterial strain | Gene region |
| --- | --- |
| Streptococcus pneumoniae | LytA |
| Haemophilus influenzae | DnaJ |
| Mycoplasma pneumoniae | DnaJ1 |
| Legionella pneumophila | DnaJ |
| Chlamydophilia pneumoniae | DnaJ1 |
| Pseudomonas aeruginosa | DnaJ |
| Klebsiella pneumoniae | DnaJ |
| Staphylococcus aureus | spaA |
| Staphylococcus aureus (MRSA) | mecA |
| Moraxella catarrhalis | DnaJ |

In order to select sequences of 20 to 30 bases in length as probe candidates directed to the amplified single-stranded nucleic acid from the gene region described in Table 1 in each pneumonia bacterium, analysis was conducted using sequence information analysis software DNASIS pro (registered trademark) (manufactured by Hitachi Software Engineering Co., Ltd.) to determine oligonucleotide probes having the sequence represented by any of SEQ ID NOs: 1 to 20.

[Preparation of First Probe-Bound Labeled High Molecular Carrier]

In order to bind oligonucleotide probes to carboxyl group-containing polystyrene latex, an amino group was introduced to the respective 5' ends of the probe sequences to synthesize 5'-terminal amino group-containing oligonucleotides. From the 20 types of oligonucleotides consisting of the sequence thus selected, 5'-terminal amino group-containing oligonucleotides were prepared as first probe sequences for the pneumonia bacteria. The nucleotides having the first probe sequences for at least three types, preferably at least five types of targeting pneumonia bacteria, were mixed with carboxyl group-containing polystyrene latex (manufactured by Bangs Laboratories, Inc.) and water-soluble carbodiimide in a 50 mM MES (2-morpholinoethanesulfonic acid, monohydrate) (manufactured by Dojindo Laboratories) buffer solution to bind carboxyl groups in the latex to amino groups in the plural types of first probes. Then, the mixture was further reacted by the addition of monoethanolamine (manufactured by Wako Pure Chemical Industries, Ltd.). The reaction solution was centrifuged, followed by removal of the supernatant. The obtained precipitate was washed and resuspended with a HEPES (2-[4-(2-hydroxyethyl)-1-piperazinyl]ethanesulfonic acid) (manufactured by Saikyo Kasei Co., Ltd.) buffer solution containing a nonionic surfactant to prepare a labeled high molecular carrier bound to plural types of nucleotides having the first probe sequence. This first probe-bound labeled high molecular carrier was stored at 4° C. until use.

[Preparation of Developing Support on which Oligonucleotides Having Second Probe Sequence were Immobilized at their Respective Predetermined Positions Distinguishable Among Pneumonia Bacteria]

In order to bind the oligonucleotides consisting of the second probe sequences selected above to a carboxyl group-modified nylon membrane (manufactured by Pall Corp.), 3'-terminal amino group-containing oligonucleotides (second probe) in which an amino group was introduced to the 3' end of the selected second probe sequence were prepared using a DNA synthesizer. The membrane was activated by treatment with water-soluble carbodiimide and washing with deionized water. One type of the 3'-terminal amino group-containing oligonucleotide (second probe) was bound to the carboxyl group-modified nylon membrane thus activated and dried in air for 15 minutes. The membrane dried in air was treated with a Tris-based buffer solution to eliminate residual active groups. Then, the membrane was washed with deionized water and dried in air again to prepare a developing support on which the oligonucleotides having the second probe sequence were immobilized in a linear pattern at their respective predetermined positions distinguishable among the pneumonia bacteria. For three or more types of targeting pneumonia bacteria, these procedures were performed at least three times on a pneumonia bacterium basis.

The sequences with an amino group introduced at the 5' or 3' end are as described in Table 2 below. The nucleic acid chromatography of the present invention was performed for the combination of various pneumonia bacteria shown below. In this table, the symbol "L" following the name of each pneumonia bacterium represents that the probe was bound to a labeled high molecular carrier. The symbol "M" following the name of each pneumonia bacterium represents that the probe was immobilized.

| Pneumonia bacterium | Probe sequence (5'-3') |
|---|---|
| MRSA L | NH2-AGACCGAAACAATGTGGAATTGGC |
| MRSA M | ATGCAGAAAGACCAAAGCATACATAT-NH2 |
| Pseudomonas aeruginosa L | NH2-GGTGACCGGTGTGGTGCCGG |
| Pseudomonas aeruginosa M | GTCTTGCAACCGACCAGGGTCGGCA-NH2 |
| Haemophilus influenza L | NH2-AAACTTGTCCGCATTGCCACGGTTC |
| Haemophilus influenza M | CTCTGGGGCTGAAAAAGGTTCTAAAG-NH2 |
| Staphylococcus aureus L | NH2-CATGATCAAACCTGGTCAAGAACTTG |
| Staphylococcus aureus M | CGGCACTACTGCTGACAAAATTGCT-NH2 |
| Streptococcus pneumoniae L | NH2-ACGCACGAGTATTGCACGAATAACC |
| Streptococcus pneumoniae M | TGCCGAAAACGCTTGATACAGGGAGT-NH2 |
| Chlamydophila pneumoniae L | NH2-ATCTTGTGAAACCTGTTCTGGTCAA |
| Chlamydophila pneumoniae M | TCAAGGGATTAAATCCTGCGAACGT-NH2 |
| Klebsiella pneumoniae L | NH2-GTGGTGGAGACGCCGGTGGGGCTGA |
| Klebsiella pneumoniae M | TGAAACCCAGACCGGCAAGCTGTTC-NH2 |
| Legionella pneumophila L | NH2-GAAGTTGAAATTACCGTTCCAAGAC |
| Legionella pneumophila M | CAATTGACCCTTGAAGAAGCAGCTA-NH2 |
| Moraxella catarrhais L | NH2-GGTTGCGCGTTTTTCAGGATCACTG |
| Moraxella catarrhais M | CCACCAGAGCCCATGCCTTGTTCAT-NH2 |
| Mycoplasma pneumoniae L | NH2-AGGCCAAACACAAGTGTAAGACTTG |
| Mycoplasma pneumoniae M | AGAATCAACGCTCCATCTTTGGTAC-NH2 |

[Reference Line]

The reference line is a line that is detected for the purpose of demonstrating that the labeled high molecular carrier can flow on a chromatography strip in order to show that the absence of a detected nucleic acid is responsible for a lack of a line at the detection position of each pneumonia causative bacterium. Since this line is detected for the purpose of confirming the flow of the labeled high molecular carrier, it is preferred that the reference line should be detected even in the presence of the detected pneumonia causative bacterium-derived nucleic acid.

[Preparation of Test Strip for Nucleic Acid Chromatography]

The test strip for nucleic acid chromatography used in the present invention was prepared as follows: the labeled high molecular carrier bound to the plural types of nucleotides having the first probe sequences for the pneumonia bacteria was dissolved in a buffer solution. The solution was applied to a developing pad (manufactured by Advantec Toyo Kaisha, Ltd.) and then dried to prepare a retainer. The retainer was connected to one end of the developing support so that the retainer did not overlap with the developing support. An absorbent pad (manufactured by Advantec Toyo Kaisha, Ltd.) was further connected to the other end of the developing support to prepare a test strip for nucleic acid chromatography.

[Confirmation of Nonspecific Binding of First Probe Bound to Labeled High Molecular Carrier]

Figure 14:
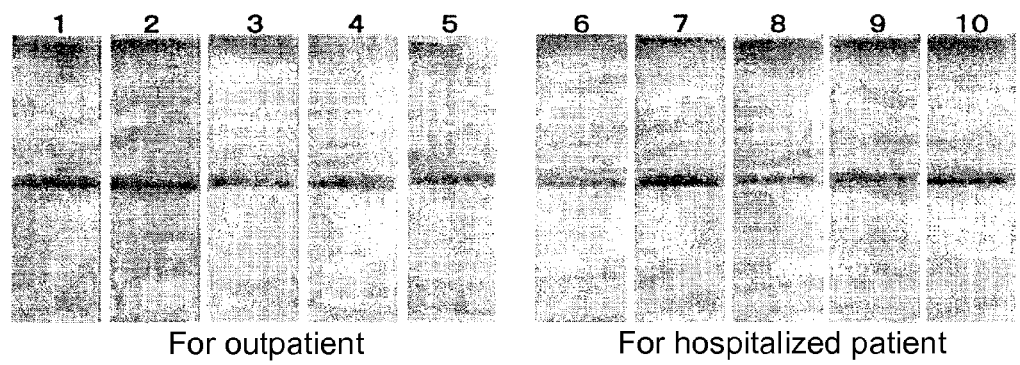
FIG. 14 is a diagram showing results of studying the nonspecific binding between respective pneumonia bacterium-specific probes.

A probe set for outpatients directed to five types of pneumonia causative bacteria allegedly particularly effective for identifying pneumonia bacteria in outpatients and a probe set for hospitalized patients directed to five types of pneumonia causative bacteria allegedly particularly effective for identifying pneumonia bacteria in hospitalized patients were tested in the absence of amplification products to check whether or not specific binding occurred due to direct hybridization between the first probe bound to the labeled high molecular carrier and the second probe (exclusive use) for each pneumonia bacterium. The first probe-bound labeled high molecular carriers used were a first probe-bound labeled high molecular carrier in which five types of first probes directed to the targeting pneumonia bacteria for outpatients were bound to the labeled high molecular carrier and a first probe-bound labeled high molecular carrier in which five types of first probes directed to the targeting pneumonia bacteria for hospitalized patients were bound to the labeled high molecular carrier. The second probe-carrying developing supports used were five second probe-carrying developing supports (exclusive use) respectively carrying five types of second probes directed to the targeting pneumonia bacteria for outpatients and five second probe-carrying developing supports (exclusive use) respectively carrying five types of second probes directed to the targeting pneumonia bacteria for hospitalized patients. The results are shown in FIG. 14. For All the bacterial strains subjected to the experiment, a red-colored line was observed at the reference position, demonstrating that nonspecific binding does not occur between the first probe bound to the labeled high molecular carrier and the second probe in the absence of amplification products.

[Detection of Target NASBA Products by Nucleic Acid Chromatography]

Figure 15:
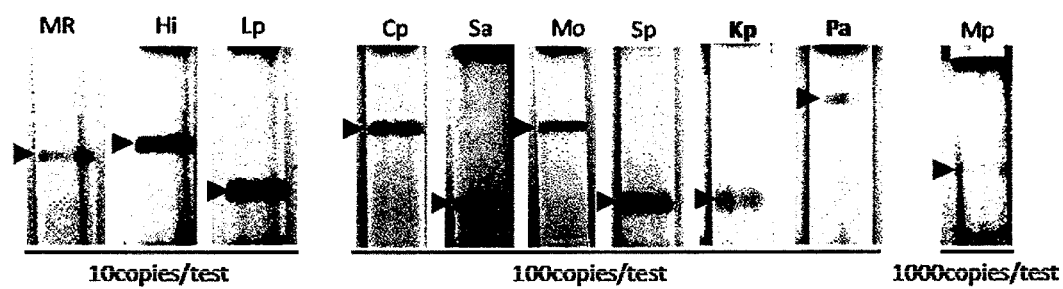
FIG. 15 is a diagram showing that target RNA amplification products were detected by nucleic acid chromatography for *Legionella pneumophila, Pseudomonas aeruginosa, Klebsiella pneumoniae*, MRSA, *Haemophilus influenzae, Staphylococcus aureus, Streptococcus pneumoniae, Moraxella catarrhalis, Mycoplasma pneumoniae*, and *Chlamydophila pneumoniae* after individual RNA amplification by the NASBA method using a primer pair directed to each bacterium.

NASBA products amplified with the primers for each bacterium were detected by nucleic acid chromatography for *Legionella pneumophila, Pseudomonas aeruginosa, Klebsiella pneumoniae*, MRSA, *Haemophilus influenzae, Staphylococcus aureus, Streptococcus pneumoniae, Moraxella catarrhalis, Mycoplasma pneumoniae*, and *Chlamydophila pneumoniae*. A test strip for chromatography was prepared according to the method described above for each individual targeting pneumonia bacterium using the probes shown in Table 2. The results are shown in FIG. 15. All the NASBA products were successfully detected using the nucleic acid chromatography strip bound to the probes for exclusive use in each pneumonia bacterium.

(Verification of Specificity of Each Probe)

The presence or absence of nonspecific reaction of each probe with the NASBA product of a bacterium other than its target was verified. The results are shown in FIG. 16. Nonspecific reaction was not observed for all the probes of this case.

(Detection by Nucleic Acid Chromatography of NASBA Products Amplified with Multiplex Primers)

Figure 17:
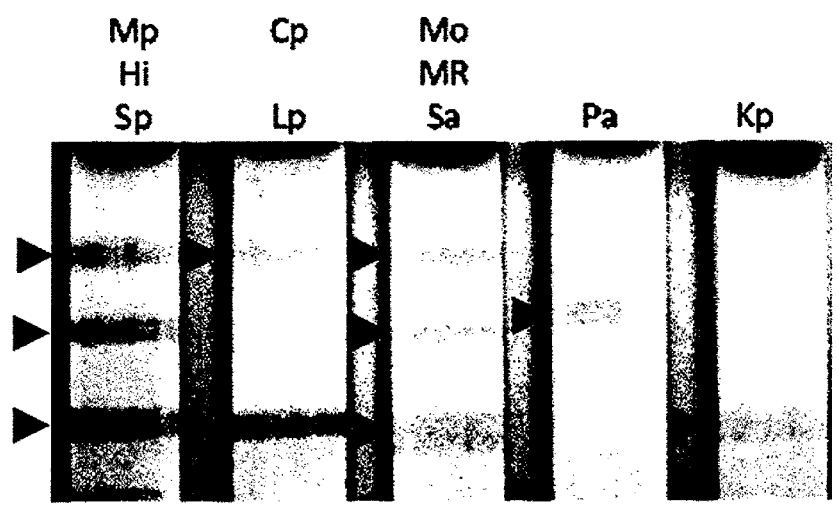
FIG. 17 is a diagram showing that target RNA amplification products were detected by nucleic acid chromatography for *Legionella pneumophila, Pseudomonas aeruginosa, Klebsiella pneumoniae*, MRSA, *Haemophilus influenzae, Staphylococcus aureus, Streptococcus pneumoniae, Moraxella catarrhalis, Mycoplasma pneumoniae*, and *Chlamydophila pneumoniae* after the RNA amplification by the NASBA method using multiplex primers including a primer pair directed to each bacterium.

NASBA products amplified with multiplex primers including the primer pairs of this case were detected by nucleic acid chromatography for *Legionella pneumophila, Pseudomonas aeruginosa, Klebsiella pneumoniae*, MRSA, *Haemophilus influenzae, Staphylococcus aureus, Streptococcus pneumoniae, Moraxella catarrhalis, Mycoplasma pneumoniae*, and *Chlamydophila pneumoniae*. The results are shown in FIG. 17. All the NASBA products amplified using the multiplex primers were successfully detected by nucleic acid chromatography.

[Detection of Plural Types of Pneumonia Bacteria]

Figure 18:
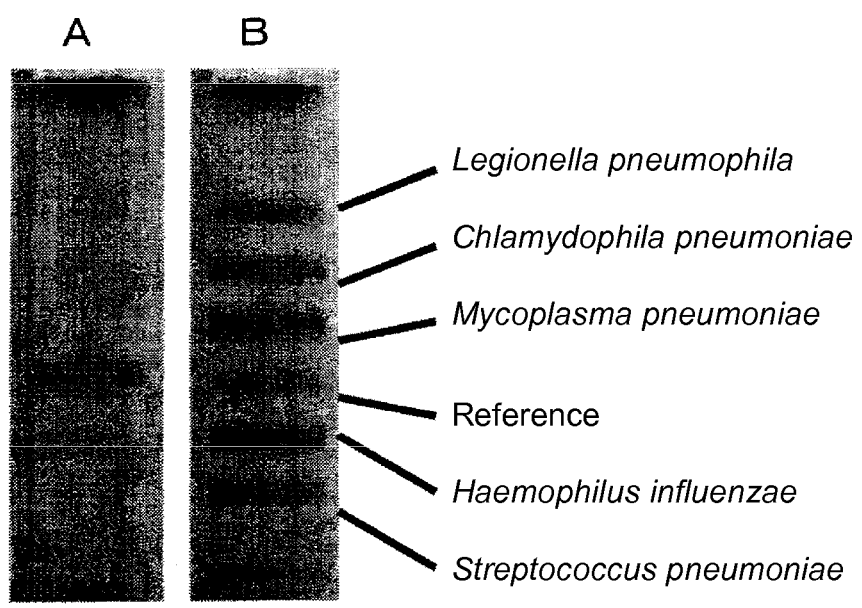
FIG. 18 is a diagram showing results of subjecting five strains of pneumonia causative bacteria to a test strip for nucleic acid chromatography of the present invention.

*Legionella pneumophila* was cultured at 35° C. in a BCYEα medium. *Chlamydophila pneumoniae* was cultured using HEp-2 cells. *Mycoplasma pneumoniae* was cultured at 37° C. in a PPLO medium. *Haemophilus influenzae* was cultured at 37° C. in a chocolate medium. *Streptococcus pneumoniae* was cultured at 37° C. in a sheep blood medium. After the culture, the nucleic acid of each sample was extracted from 100 μL of its bacterial suspension using EXTRAGEN II reagent (manufactured by Tosoh Corp.). The nucleic acids derived from the five types of bacterium were dissolved with 50 μL of RNase-free water. 2.5 μL of each nucleic acid solution was subjected to NASBA amplification reaction with total RNA as a template using NASBA Amplification kit (manufactured by KAINOS Laboratories, Inc.) and respective bacterial strain-specific primer pairs hybridizing to sequences in their respective target regions of 10 bacterial strains differing from the sequences hybridized by the set of probe pairs of the present invention. In this case, the concentration of the primers for exclusive use in each bacterium was adjusted to 0.2 μM in terms of the final concentration. After the amplification reaction, the respective solutions of the bacteria were combined without pretreating NASBA amplification products after the completion of amplification. Immediately, an attempt was made to detect pneumonia bacteria by nucleic acid chromatography using the nucleic acid chromatography strip. When the NASBA products were not allowed to flow, only the reference line indicating that flow was performed was detected (see FIG. 18A). When the NASBA products from the five strains of pneumonia causative bacteria were allowed to flow, lines were detected at their respective detection positions aside from the reference line (see FIG. 18B).

The invention claimed is:

1. A method for detecting pneumonia causative bacteria targeting at least three types of pneumonia bacteria selected from *Streptococcus pneumoniae, Haemophilus influenzae, Mycoplasma pneumoniae, Chlamydophila pneumoniae, Legionella pneumophila, Klebsiella pneumoniae, Pseudomonas aeruginosa, Moraxella catarrhalis*, methicillin-resistant *Staphylococcus aureus* (MRSA), and *Staphylococcus aureus*, the method comprising the following steps (a) to (f):

1) step (a) of amplifying a pneumonia bacterium-specific target nucleic acid arbitrarily extracted from a sample as a single-stranded nucleic acid, using a set of at least three types of NASBA multiplex primer pairs differing by the pneumonia bacteria;
2) step (b) of preparing at least three types of probe pairs differing by the pneumonia bacteria, wherein the probe pairs are selected from a nucleotide sequence complementary to an amplification product;
3) step (c) of binding a first probe for the at least three types of pneumonia bacteria to a one labeled high molecular carrier to prepare a first probe-bound labeled high molecular carrier;
4) step (d) of immobilizing a second probe for the at least three types of pneumonia bacteria paired with the first probe, to a predetermined position distinguishable for each of the pneumonia bacteria to prepare a second probe-carrying developing support;
5) step (e) of hybridizing the amplification product with the second probe carried by the developing support and the first probe bound to the labeled high molecular carrier, followed by a detection; and
6) step (f) of evaluating and assessing the detection image, and wherein the set of at least three types of NASBA multiplex primer pairs differing by the pneumonia bacteria used in the above step (a) is selected from a primer pair represented by any one of the following (i) to (x), or a primer set capable of amplifying a pneumonia bacterium-specific target nucleic acid, constituted of a nucleotide sequence in which 1 to 3 bases are deleted, substituted or added in the nucleotide sequence represented by SEQ ID NOs: 21 to 40 constituting the primer pair:

(i) a forward primer consisting of the nucleotide sequence represented by SEQ ID NO: 21 and a reverse primer consisting of the nucleotide sequence represented by SEQ ID NO: 31 and an RNA polymerase promoter sequence added to the 5' end thereof;
(ii) a forward primer consisting of the nucleotide sequence represented by SEQ ID NO: 22 and a reverse primer consisting of the nucleotide sequence represented by SEQ ID NO: 32 and an RNA polymerase promoter sequence added to the 5' end thereof;
(iii) a forward primer consisting of the nucleotide sequence represented by SEQ ID NO: 23 and a reverse primer consisting of the nucleotide sequence represented by SEQ ID NO: 33 and an RNA polymerase promoter sequence added to the 5' end thereof;
(iv) a forward primer consisting of the nucleotide sequence represented by SEQ ID NO: 24 and a reverse primer consisting of the nucleotide sequence represented by SEQ ID NO: 34 and an RNA polymerase promoter sequence added to the 5' end thereof;
(v) a forward primer consisting of the nucleotide sequence represented by SEQ ID NO: 25 and a reverse primer consisting of the nucleotide sequence represented by SEQ ID NO: 35 and an RNA polymerase promoter sequence added to the 5' end thereof;
(vi) a forward primer consisting of the nucleotide sequence represented by SEQ ID NO: 26 and a reverse primer consisting of the nucleotide sequence represented by SEQ ID NO: 36 and an RNA polymerase promoter sequence added to the 5' end thereof;
(vii) a forward primer consisting of the nucleotide sequence represented by SEQ ID NO: 27 and a reverse primer consisting of the nucleotide sequence represented by SEQ ID NO: 37 and an RNA polymerase promoter sequence added to the 5' end thereof;
(viii) a forward primer consisting of the nucleotide sequence represented by SEQ ID NO: 28 and a reverse primer consisting of the nucleotide sequence represented by SEQ ID NO: 38 and an RNA polymerase promoter sequence added to the 5' end thereof;
(ix) a forward primer consisting of the nucleotide sequence represented by SEQ ID NO: 29 and a reverse primer consisting of the nucleotide sequence represented by SEQ ID NO: 39 and an RNA polymerase promoter sequence added to the 5' end thereof; and
(x) a forward primer consisting of the nucleotide sequence represented by SEQ ID NO: 30 and a reverse primer consisting of the nucleotide sequence represented by SEQ ID NO: 40 and an RNA polymerase promoter sequence added to the 5' end thereof.

2. The detection method according to claim 1, wherein the first probe for the at least three types of pneumonia bacteria consists of at least three types of DNAs selected from the nucleotide sequences represented by SEQ ID NOs: 1 to 10, and the second probe for the at least three types of pneumonia bacteria to be paired with the first probe is at least three types of DNAs selected from the nucleotide sequences represented by SEQ ID NOs: 11 to 20.

3. A kit for detecting pneumonia causative bacteria targeting at least three types of pneumonia bacteria selected from *Streptococcus pneumoniae, Haemophilus influenzae, Mycoplasma pneumoniae, Chlamydophila pneumoniae, Legionella pneumophila, Klebsiella pneumoniae, Pseudomonas aeruginosa, Moraxella catarrhalis*, methicillin-resistant *Staphylococcus aureus* (MRSA), and *Staphylococcus aureus*, the kit comprising
1) at least three types of NASBA multiplex primer pairs differing by the pneumonia bacteria, selected from a primer pair represented by any one of the following (xi) to (xx) which are capable of amplifying a pneumonia bacterium-specific target nucleic acid arbitrarily extracted from a sample, or a primer pair capable of amplifying a pneumonia bacteria-specific target nucleic acid, constituted of a nucleotide sequence in which 1 to 3 bases are deleted, substituted or added in the nucleotide sequence shown by SEQ ID NOs: 21 to 40 constituting the primer pair,
   (xi) a forward primer consisting of the nucleotide sequence represented by SEQ ID NO: 21 and a reverse primer consisting of the nucleotide sequence represented by SEQ ID NO: 31 and an RNA polymerase promoter sequence added to the 5' end thereof;
   (xii) a forward primer consisting of the nucleotide sequence represented by SEQ ID NO: 22 and a reverse primer consisting of the nucleotide sequence represented by SEQ ID NO: 32 and an RNA polymerase promoter sequence added to the 5' end thereof;
   (xiii) a forward primer consisting of the nucleotide sequence represented by SEQ ID NO: 23 and a reverse primer consisting of the nucleotide sequence represented by SEQ ID NO: 33 and an RNA polymerase promoter sequence added to the 5' end thereof;
   (xiv) a forward primer consisting of the nucleotide sequence represented by SEQ ID NO: 24 and a reverse primer consisting of the nucleotide sequence represented by SEQ ID NO: 34 and an RNA polymerase promoter sequence added to the 5' end thereof;
   (xv) a forward primer consisting of the nucleotide sequence represented by SEQ ID NO: 25 and a reverse primer consisting of the nucleotide sequence represented by SEQ ID NO: 35 and an RNA polymerase promoter sequence added to the 5' end thereof;
   (xvi) a forward primer consisting of the nucleotide sequence represented by SEQ ID NO: 26 and a reverse primer consisting of the nucleotide sequence represented by SEQ ID NO: 36 and an RNA polymerase promoter sequence added to the 5' end thereof;
   (xvii) a forward primer consisting of the nucleotide sequence represented by SEQ ID NO: 27 and a reverse primer consisting of the nucleotide sequence represented by SEQ ID NO: 37 and an RNA polymerase promoter sequence added to the 5' end thereof;
   (xviii) a forward primer consisting of the nucleotide sequence represented by SEQ ID NO: 28 and a reverse primer consisting of the nucleotide sequence represented by SEQ ID NO: 38 and an RNA polymerase promoter sequence added to the 5' end thereof;
   (xix) a forward primer consisting of the nucleotide sequence represented by SEQ ID NO: 29 and a reverse primer consisting of the nucleotide sequence represented by SEQ ID NO: 39 and an RNA polymerase promoter sequence added to the 5' end thereof; and
   (xx) a forward primer consisting of the nucleotide sequence represented by SEQ ID NO: 30 and a reverse primer consisting of the nucleotide sequence represented by SEQ ID NO: 40 and an RNA polymerase promoter sequence added to the 5' end thereof, further comprising
2) a first probe-bound labeled high molecular carrier in which a first probe for the at least three types of pneumonia bacteria differing by the pneumonia bacteria is bound to a labeled high molecular carrier, wherein the first probe is selected from a nucleotide sequence complementary to an amplification product; and
3) a second probe-carrying developing support in which a second probe for the at least three types of pneumonia bacteria to be paired with the first probe is immobilized at a predetermined positions distinguishable for each of the pneumonia bacteria.

4. The kit according to claim 3, wherein the first probe for the at least three types of pneumonia bacteria consists of at least three types of DNAs selected from the nucleotide sequences represented by SEQ ID NOs: 1 to 10, and the second probe for the at least three types of pneumonia bacteria to be paired with the first probe is at least three types of DNAs selected from the nucleotide sequences represented by SEQ ID NOs: 11 to 20.

\* \* \* \* \*

UNITED STATES PATENT AND TRADEMARK OFFICE
CERTIFICATE OF CORRECTION

PATENT NO. : 9,347,944 B2
APPLICATION NO. : 13/637815
DATED : May 24, 2016
INVENTOR(S) : Mutsunori Shirai et al.

It is certified that error appears in the above-identified patent and that said Letters Patent is hereby corrected as shown below:

In the specification,

Col. 17, line 16, "in air for minutes;" should be --in air for 15 minutes--.

In the claims,

Col. 43, claim 1, line 38, "bacteria to a one" should be --bacteria to one--.

Signed and Sealed this
Nineteenth Day of July, 2016

Michelle K. Lee
*Director of the United States Patent and Trademark Office*